US006218549B1

(12) United States Patent
Horne et al.

(10) Patent No.: US 6,218,549 B1
(45) Date of Patent: Apr. 17, 2001

(54) BICYCLIC AMINOIMIDAZOLES

(75) Inventors: David A. Horne; Kenichi Yakushijin, both of New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/441,721

(22) Filed: Nov. 16, 1999

Related U.S. Application Data

(62) Division of application No. 09/185,831, filed on Nov. 4, 1998, which is a continuation of application No. 08/540,554, filed as application No. PCT/US94/03883 on Apr. 8, 1994, now Pat. No. 5,834,609, which is a continuation-in-part of application No. 08/044,639, filed on Apr. 8, 1993, now abandoned.

(51) Int. Cl.[7] ........................ C07D 405/00; C07D 207/00
(52) U.S. Cl. ............................................ 548/517; 548/537
(58) Field of Search ..................................... 548/517, 537

(56) References Cited

U.S. PATENT DOCUMENTS

| | | | |
|---|---|---|---|
| 3,746,705 | 7/1973 | Cavalleri et al. | 260/240 |
| 4,812,462 | 3/1989 | Blankley et al. | 471/4 |
| 5,091,390 | 2/1992 | Ardecky et al. | 514/303 |
| 5,621,099 | 4/1997 | Annovra et al. | 540/521 |

FOREIGN PATENT DOCUMENTS

| | | |
|---|---|---|
| 2016437 | 11/1990 | (CA) . |
| WO8707274 | 12/1987 | (WO) . |

OTHER PUBLICATIONS

Abstract. Xu et al. (Tetrahedron Lett. (1994), 35(3), 351–4.*

Braun, M., et al., Journal of the American Chemical Society (1978), "Synthesis of Parazoanthoxanthins and Pseudozoanthoxanthins," vol. 100, pp. 4208–4213; U.S.A.

Braun, M., et al., Journal of the American Chemical Society (1976), "Synthesis of Zoanthoxanthins," vol. 32, pp. 3049–3050; U.S.A.

Colson, Genevieve et al., "Mode of Action of the Antitumor Compound Girodazole", Chemical Abstracts 117: 82994y, (1992).

Commercon, A., et al., Tetrahedron Letters (1991), "A Diastereoselective Synthesis of Girolline," vol. 32, pp. 1419–1422; U.K.

Dalkafouki, A., et al., Tetrahedron Letters (1991), "Sysnthesis of 2–Dimethylaminoimidazole Derivatives: A New Access to Indolyl–imidazole Alkaloids of Marine Origina," vol. 32 pp., 5325–5328; U.K.

Fernandez–Bolanos, J., et al., "Synthesis of 1–Alkyl (or H) –4–(D–lyxo–tetritol–l–yl) –4–imidazolin–2–ylideneammonium Picrates and Chlorides" Chemical Abstracts 116: 255934p, (1992).

Grimmett, M.R., "imidazoles and their Benzo Derivatives: (ii) Reactivity," in Comprehensive Heterocyclic Chemistry: The Structure, Reactions, Synthesis and Uses Heterocyclic Compounds, Potts, K.T., et.; Pergamon Press, New York (1984), vol. 5, pp. 404–405; U.S.A.

Kobayaski, J., et al., "α–Adrenoceptor blocking action of hymenin, a novel marine alkaloid ", Chemical Abstracts, 108(15): 124371q (1988).

Kobayaski, J., et al., "α–Adrenoceptor blocking action of hymenin, a novel marine alkaloid", Experientia 44(1), pp. 86–87 (1988).

Lancini, G., et al., United Kingdon patent 1,132,013, "Imidazole Derivatives," published Oct. 30, 1968.

Lancini, G., et al., Journal of Heterocyclic Chemistry (1966), "A New Synthesis of Alkyl and Aryl 2–Amino–imidazoles," vol. 3, pp. 152–154; U.S.A.

Ruccia, M., et al, Tetrahedron (1974), "Mononuclear Heterocyclic Rearrangements–VI: Conversion of 1,2,4–Oxadiazoles into Imidazoles," vol. 30, pp. 3859–3864; U.K.

Walker, R., et al, Journal of the American Chemical Society (1981), "Sceptrin, an Antimicrobia Agent from the sponge Agelas Sceptrum," vol. 103, pp. 6772–6773; U.S.A.

Xu, Y., et al., "Reactions 2–Aminoimidazoles with Aldehydes. Hydroxyalkylation and Cycloaddition", Tetrahedron Letters (1993), 34(44):6981–6984.

Zurita, M., et al., Tetrahedron Letters (1991), "A Diastereoselective Synthesis of Girolline," vol. 45, pp. 6713–6720; U.K.

Supriyono, A. et al. (1995) "Bioactive Alkaloids from the Tropical Marine Sponge Axinella carteri," Naturforsch 50:669–674.

* cited by examiner

*Primary Examiner*—Bruce Kifle
(74) *Attorney, Agent, or Firm*—John P. White; Cooper & Dunham LLP

(57) ABSTRACT

The subject invention provides a bicyclic aminoimidazole compound, a hydroxyalkyl aminoimidazole compound, a bicyclic pyrrole compound, a hymenin compound, an aldehyde aminoimidazole compound, a ketal aminoimidazole compound, a tricyclic compound, and a tetrahydropurine compound. The subject invention also provides for processes for preparing the compounds.

15 Claims, 10 Drawing Sheets

I.

(1)

(5) + (6)

II.

(2)

(7)

III.

(3)

(8)

IV.

(4)

(9)

(10)

V.

(11) (12) (13) (14) (15)

(±) - Hymenin (16)

VI.

(1) + (14)

(±) - Hymenin (16)

(15) (17)

(18)

(8) R = alkyl or aryl (19)

(9) R = $CH_2CH_2NH_2$ or aryl (20)

BICYCLIC AMINOIMIDAZOLES

This application is a divisional of U.S. Ser. No. 09/185,831, filed Nov. 4, 1998, which is a continuation of U.S. Ser. No. 08/540,554, filed Oct. 6, 1995, now U.S. Pat. No. 5,834,609, issued Nov. 10, 1998, which is a continuation-in-part of PCT International Application No. PCT/US94/03883, filed on Apr. 8, 1994, which was a continuation-in-part of U.S. Ser. No. 08/044,639, filed Apr. 8, 1993, now abandoned.

BACKGROUND OF THE INVENTION

Throughout this application various patents and publications are referenced and citations are provided in parentheses. The disclosure of these patents and publications in their entireties are hereby incorporated by reference into this application in order to more fully describe the state of the art to which this invention pertains.

Many marine natural products contain the 2-aminoimidazole substructure. Certain members of this class of compounds appear to be biogenetically related, having diverged from a common, yet unidentified intermediate. Since the majority of these marine products have been isolated from depths ranging from 30 to 800 meters below sea level, metabolite availability has been a problem for chemical and biochemical investigations. Minute amounts contained in the marine source make it impractical to obtain suitable quantities of material necessary for further study. The present invention provides versatile and efficient methods of synthesizing these metabolites, and provides access to new compounds derived therefrom with anti-cancer, anti-hypertensive, anti-microbial and anti-viral properties. Certain new compounds are useful to treat central nervous system disorders such as shock, Parkinson's disease and ischemia.

SUMMARY OF THE INVENTION

The subject invention provides a bicyclic aminoimidazole compound having the structure

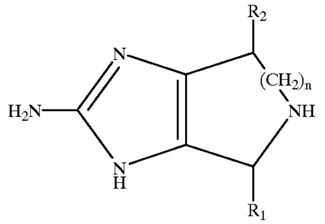

wherein n is an integer from 0 to about 5;

wherein $R_1$ is H; a $C_1$ to about $C_{10}$ alkyl group, which is a primary alkyl group, or a secondary branched alkyl group, or a tertiary branched alkyl group wherein the tertiary carbon of the tertiary branched alkyl group is separated from the ring structure of the bicyclic aminoimidazole compound by at least one carbon atom; a phenyl group; a thiophenyl group; a pyrrolyl group; a furanyl group; a benzyl group; or a pyridyl group;

which alkyl, phenyl, thiophenyl, pyrrolyl, furanyl, benzyl, or pyridyl groups are substituted or unsubstituted; and wherein $R_2$ is H; a $C_1$ to about $C_{10}$ alkyl group, which is a straight chain alkyl group, or a branched alkyl group; or a phenyl group; which alkyl or phenyl groups are substituted or unsubstituted.

The subject invention provides a hydroxyalkyl aminoimidazole compound having the structure

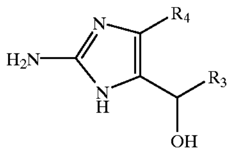

wherein;

when $R_3$ is a substituted $C_1$ alkyl group; a $C_2$ to about $C_{10}$ alkyl group, which is a primary alkyl group, a secondary branched alkyl group, or a tertiary branched alkyl group wherein the tertiary carbon of the tertiary branched alkyl group is separated from the ring structure of the hydroxyalkyl aminoimidazole compound by at least one carbon atom, which alkyl groups are substituted or unsubstituted;

then $R_4$ is H; a $C_1$ to about $C_{10}$ straight chain alkyl group or branched alkyl group to which guanidine is attached wherein the guanidine is separated from the ring structure of the hydroxyalkyl aminoimidazole compound by at least one carbon atom; a $C_1$ to about $C_{10}$ straight chain alkyl group or branched alkyl group; a phenyl group; a thiophenyl group; a pyrrolyl group; a furanyl group; a benzyl group; or a pyridyl group; which alkyl to which guanidine is attached, alkyl, phenyl, thiophenyl, pyrrolyl, furanyl, benzyl, or pyridyl groups are substituted or unsubstituted; or;

when $R_3$ is H;

then $R_4$ is a $C_1$ to about $C_{10}$ straight chain alkyl group or branched alkyl group to which guanidine is attached wherein the guanidine is separated from the ring structure of the hydroxyalkyl aminoimidazole compound by at least one carbon atom; a $C_1$ to about $C_{10}$ straight chain alkyl group or branched alkyl group; a phenyl group; a thiophenyl group; a pyrrolyl group; a furanyl group; a benzyl group; or a pyridyl group; which alkyl to which guanidine is attached, alkyl, phenyl, thiophenyl, pyrrolyl, furanyl, benzyl, or pyridyl groups are substituted or unsubstituted.

The subject invention provides a bicyclic pyrrole compound having the structure

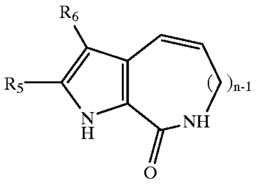

wherein n is an integer from 1 to about 6;

wherein $R_5$ and $R_6$ are the same or different, and are H; a $C_1$ to about $C_{10}$ straight chain alkyl group or branched alkyl group, which alkyl groups are substituted or unsubstituted; or halogen.

The subject invention provides a hymenin compound having the structure

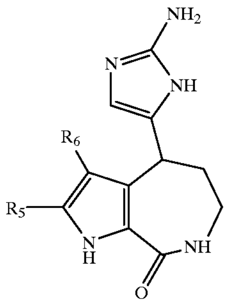

wherein $R_5$ and $R_6$ are the same or different, and are H; a $C_1$ to about $C_{10}$ straight chain alkyl group or branched alkyl group, which alkyl group is substituted or unsubstituted; or F, Cl, or I.

The subject invention provides an aldehyde aminoimidazole compound having the structure

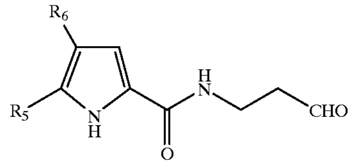

wherein $R_5$ and $R_6$ are the same or different, and are H; a $C_1$ to about $C_{10}$ straight chain alkyl group or branched alkyl group, which alkyl group is substituted or unsubstituted; or halogen.

The subject invention provides a ketal aminoimidazole compound having the structure

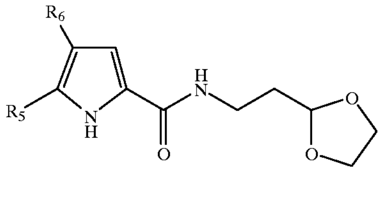

wherein $R_5$ and $R_6$ are the same or different, and are H; a $C_1$ to about $C_{10}$ straight chain alkyl group or branched alkyl group, which alkyl group is substituted or unsubstituted; or halogen.

The subject invention provides a tricyclic compound having the structure

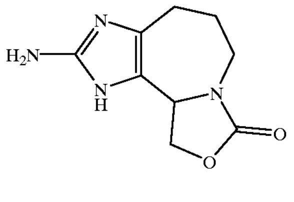

The subject invention provides a tetrahydropurine compound having the structure

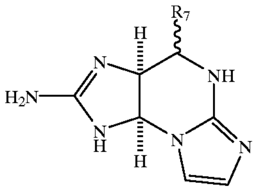

wherein $R_7$ is a $C_1$ to about $C_{10}$ alkyl group, which is a primary alkyl group, a secondary branched alkyl group, or a tertiary branched alkyl group wherein the tertiary carbon of the tertiary branched alkyl group is separated from the ring structure of the tetrahydropurine compound by at least one carbon atom, which alkyl groups are substituted or unsubstituted.

DETAILED DESCRIPTION OF THE INVENTION

Figure 1:
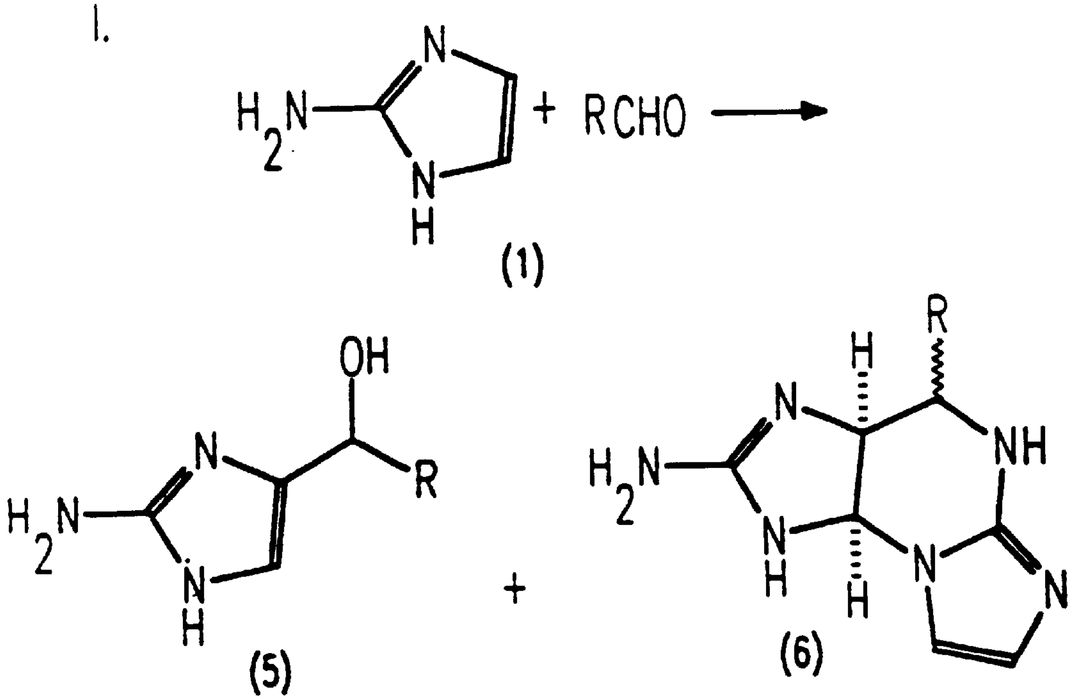
FIG. 1A outlines the reaction between 2-aminoimidazoles and aldehydes, to yield hydroxyalkylaminoizidazole (5).
FIG. 1B outlines the reaction between 2-aminoimidazoles and aldehydes, to yield hydroxyalkylaminoimidazole (7).
FIG. 1C outlines the reaction between 2-aminoimidazoles and aldehydes, to yield hydroxyalkylaminoimidazole (8).
FIG. 1D outlines the reaction between 2-aminoimidazoles and aldehydes, to yield imidazoazepines (9).
Figure 1:
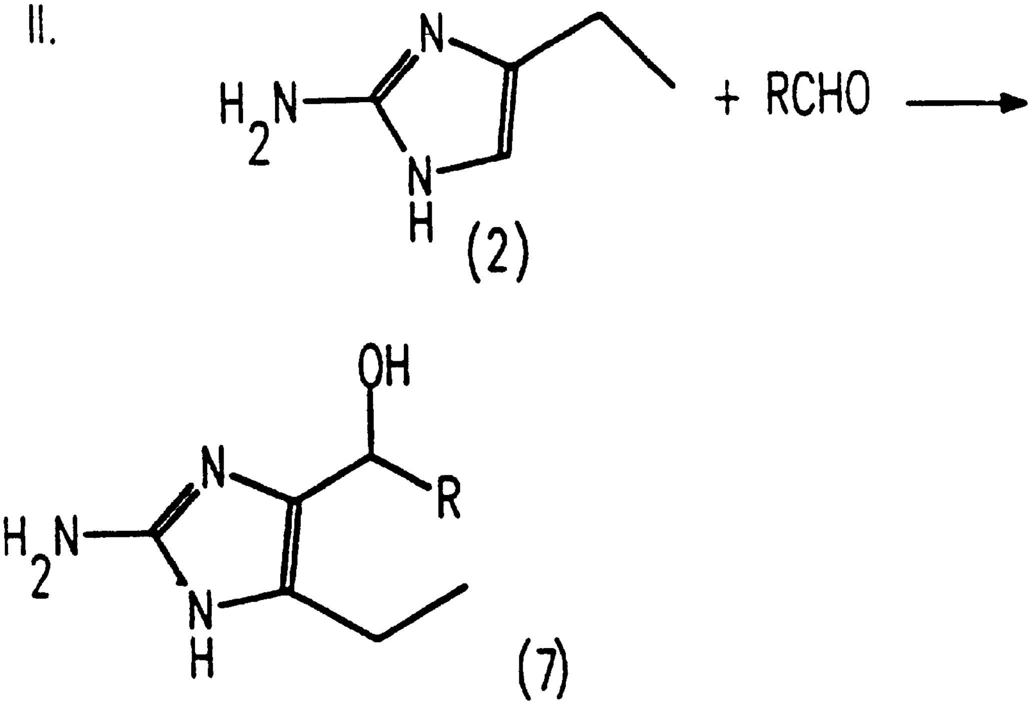
Figure 1:
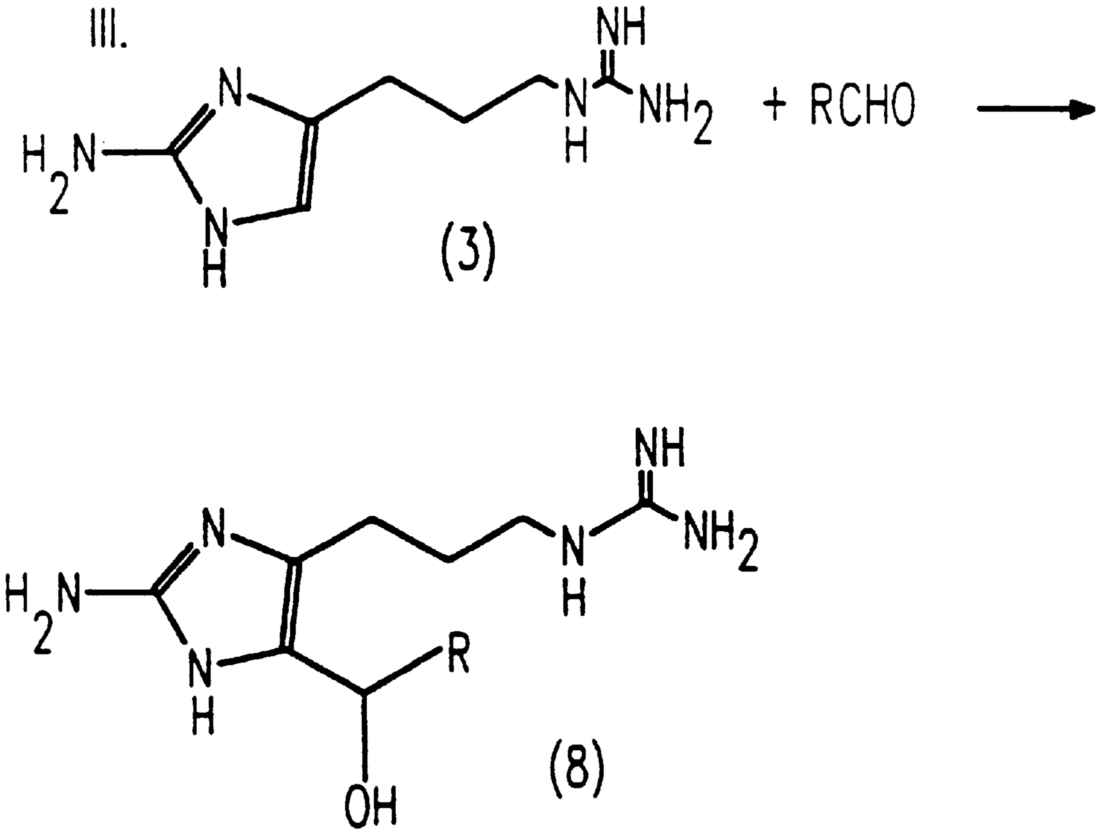
Figure 1:
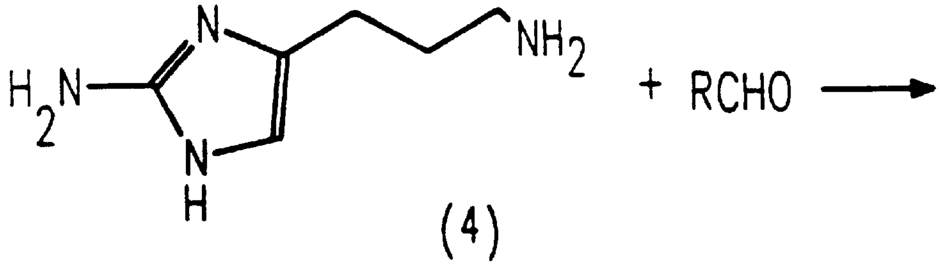
Figure 1:
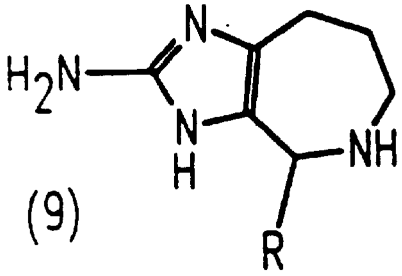
Figure 1:
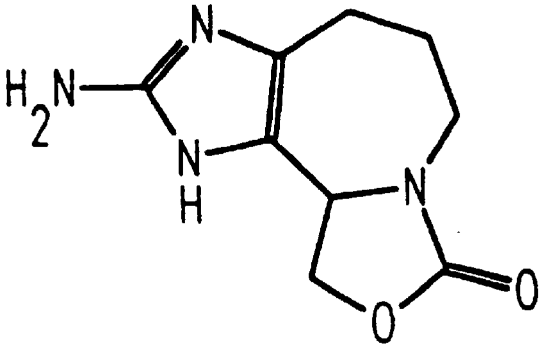

The subject invention provides a bicyclic aminoimidazole compound having the structure

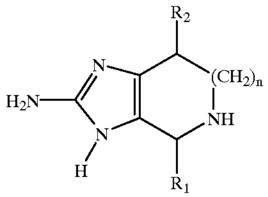

wherein n is an integer from 0 to about 5;

wherein $R_1$ is H; a $C_1$ to about $C_{10}$ alkyl group, which is a primary alkyl group, or a secondary branched alkyl group, or a tertiary branched alkyl group wherein the tertiary carbon of the tertiary branched alkyl group is separated from the ring structure of the bicyclic aminoimidazole compound by at least one carbon atom; a phenyl group; a thiophenyl group; a pyrrolyl group; a furanyl group; a benzyl group; or a pyridyl group;

which alkyl, phenyl, thiophenyl, pyrrolyl, furanyl, benzyl, or pyridyl groups are substituted or unsubstituted; and wherein $R_2$ is H; a $C_1$ to about $C_{10}$ alkyl group, which is a straight chain alkyl group, or a branched alkyl group; or a phenyl group; which alkyl or phenyl groups are substituted or unsubstituted.

The bicyclic aminoimidazole compound is useful as an anti-tumor and anti-microbial agent.

Regarding the bicyclic aminoimidazole compound of the subject invention, the subject invention provides that the alkyl, phenyl, thiophenyl, pyrrolyl, furanyl, benzyl, or pyridyl groups may be substituted with halogen, alcohol, alkoxy, dialkyl amine, alkyl aryl amine, diaryl amine, thiol, sulfide, or nitro groups.

The subject invention provides the process for preparing the bicyclic aminoimidazole compound of the subject invention, wherein $R_1$, $R_2$, and n are the same as defined above, which process comprises:

reacting one molecular equivalent of an amine aminoimidazole having the structure

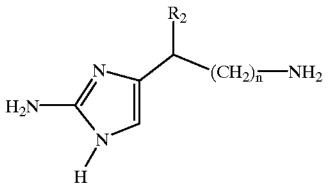

with one molecular equivalent of an aldehyde having the structure $R_1$—C(H)=0, in a polar hydroxylic solvent or a polar nonhydroxylic solvent, to form the bicyclic aminoimidazole compound.

Regarding the process for preparing the bicyclic aminoimidazole compound, the subject invention provides that the polar hydroxylic solvent may be a mixture of water and an organic polar solvent, and the volume ratio of the water and the organic polar solvent is from about 1/10 to about 10/1.

Regarding the process for preparing the bicyclic aminoimidazole compound, and further regarding the volume ratio of the water and the organic polar solvent, the subject invention provides that the volume ratio of the water and the organic polar solvent may be from about 40/60 to about 60/40.

Regarding the process for preparing the bicyclic aminoimidazole compound, and further regarding the organic polar solvent, the subject invention provides that the organic polar solvent may be methanol; ethanol; N,N-dimethylformamide; dioxane; tetrahydrofuran; dimethyl sulfoxide; or acetonitrile.

Regarding the process for preparing the bicyclic aminoimidazole compound, the subject invention provides that the polar hydroxylic solvent may be a mixture of water and methanol in a volume ratio of from about 40/60 to about 60/40; or a mixture of water and ethanol in a volume ratio of from about 40/60 to about 60/40.

Regarding the process for preparing the bicyclic aminoimidazole compound, the subject invention provides that the polar nonhydroxylic solvent may be N,N-dimethylformamide; dioxane; tetrahydrofuran; dimethyl sulfoxide; or acetonitrile.

Regarding the process for preparing the bicyclic aminoimidazole compound, the subject invention provides that the process may be performed at a temperature of about 0° C. to about 100° C.

Regarding the process for preparing the bicyclic aminoimidazole compound, the subject invention provides that the process may be performed at a temperature of about 0° C. to about 50° C.

Regarding the process for preparing the bicyclic aminoimidazole compound, the subject invention provides that the process may be performed at a temperature of about 25° C.

Regarding the process for preparing the bicyclic aminoimidazole compound, the subject invention provides that the process may be performed for a reaction time of from about 5 minutes to about 24 hours.

Regarding the process for preparing the bicyclic aminoimidazole compound, the subject invention provides that the process may be performed for a reaction time of from about 1 hour to about 5 hours. In general, the reaction time depends on the nature of the aldehyde; wherein the more hindered the aldehyde, the longer the reaction time.

The subject invention provides a hydroxyalkyl aminoimidazole compound having the structure

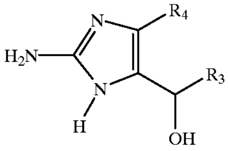

wherein;

when $R_3$ is a substituted $C_1$ alkyl group; a $C_2$ to about $C_{10}$ alkyl group, which is a primary alkyl group, a secondary branched alkyl group, or a tertiary branched alkyl group wherein the tertiary carbon of the tertiary branched alkyl group is separated from the ring structure of the hydroxyalkyl aminoimidazole compound by at least one carbon atom, which alkyl groups are substituted or unsubstituted;

then $R_4$ is H; a $C_1$ to about $C_{10}$ straight chain alkyl group or branched alkyl group to which guanidine is attached wherein the guanidine is separated from the ring structure of the hydroxyalkyl aminoimidazole compound by at least one carbon atom; a $C_1$ to about $C_{10}$ straight chain alkyl group or branched allyl group; a phenyl group; a phenyl group; a thiophenyl group; a pyrrolyl group; a furanyl group; a benzyl group; or aa pyridyl group; which alkyl to which guanidine is attached, alkyl, phenyl, thiophenyl, pyrrolyl, furanyl, benzyl, or pyridyl groups are substituted or unsubstituted; or;

when $R_3$ is H;

then $R_4$ is a $C_1$ to about $C_{10}$ straight chain alkyl group or branched alkyl group to which guanidine is attached wherein the guanidine is separated from the ring structure of the hydroxyalkyl aminoimidazole compound by at least one carbon atom; a $C_1$ to about $C_{10}$ straight chain alkyl group or branched alkyl group; a phenyl group; a thiophenyl group; a pyrrolyl group; a furanyl group; a benzyl group; or a pyridyl group; which alkyl to which guanidine is attached, alkyl, phenyl, thiophenyl, pyrrolyl, furanyl, benzyl, or pyridyl groups are substituted or unsubstituted.

The hydroxyalkyl aminoimidazole compound is useful as an anti-cancer agent and as an intermediate in the preparation of girolline analogues, also useful as anti-cancer agents.

Regarding the hydroxyalkyl aminoimidazole compound of the subject invention, the subject invention provides that the alkyl to which guanidine is attached, alkyl, phenyl, thiophenyl, pyrrolyl, furanyl, benzyl, or pyridyl groups may be substituted with halogen, alcohol, alkoxy, dialkyl amine, alkyl aryl amine, diaryl amine, thiol, or sulfide groups.

The subject invention provides the process for preparing the hydroxyalkyl aminoimidazole compound of the subject invention, wherein;

when $R_3$ is a $C_1$ to about $C_{10}$ alkyl group, which is a primary alkyl group, a secondary branched alkyl group, or a tertiary branched alkyl group wherein the tertiary carbon of the tertiary branched alkyl group is separated from the ring structure of the hydroxyalkyl aminoimidazole compound by at least one carbon atom; which alkyl groups are substituted or unsubstituted;

then $R_4$ is H, a $C_1$ to about $C_{10}$ straight chain alkyl group or branched alkyl group to which guanidine is attached wherein the guanidine is separated from the ring structure of the hydroxyalkyl aminoimidazole compound by at least one carbon atom, a $C_1$ to about $C_{10}$ straight chain alkyl group or branched alkyl group, a phenyl group, a thiophenyl group, a pyrrolyl group, a furanyl group, a benzyl group, or a pyridyl group; which alkyl to which guanidine is attached, alkyl, phenyl, thiophenyl, pyrrolyl, furanyl, benzyl, or pyridyl groups are substituted or unsubstituted; or;

when $R_3$ is H; then $R_4$ is a $C_1$ to about $C_{10}$ straight chain alkyl group or branched alkyl group to which guanidine is attached wherein the guanidine is separated from the ring structure of the hydroxyalkyl aminoimidazole compound by at least one carbon atom, a $C_1$ to about $C_{10}$ straight chain alkyl group or branched alkyl group, a phenyl group, a thiophenyl group, a pyrrolyl group, a furanyl group, a benzyl group, or a pyridyl group; which alkyl to which guanidine is attached, alkyl, phenyl, thiophenyl, pyrrolyl, furanyl, benzyl, or pyridyl groups are substituted or unsubstituted; which process comprises:

reacting one molecular equivalent of an alkyl aminoimidazole having the structure

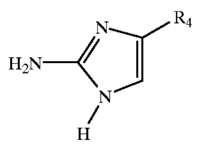

with one molecular equivalent of an aldehyde having the structure $R_3$—C(H)═0, in a polar hydroxylic solvent, to form the hydroxyalkyl aminoimidazole compound.

Regarding the process for preparing the hydroxyalkyl aminoimidazole compound, the subject invention provides that the polar hydroxylic solvent may be a mixture of water and an organic polar solvent, and the volume ratio of the water and the organic polar solvent is from about 1/10 to about 10/1.

Regarding the process for preparing the hydroxyalkyl aminoimidazole compound, and further regarding the volume ratio of the water and the organic polar solvent, the subject invention provides that the volume ratio of the water and the organic polar solvent is from about 40/60 to about 60/40.

Regarding the process for preparing the hydroxyalkyl aminoimidazole compound, and further regarding the organic polar solvent, the subject invention provides that the organic polar solvent may be methanol; ethanol; N,N-dimethylformamide; dioxane; tetrahydrofuran; dimethyl sulfoxide; or acetonitrile.

Regarding the process for preparing the hydroxyalkyl aminoimidazole compound, the subject invention provides that the polar hydroxylic solvent may be a mixture of water and methanol in a volume ratio of from about 40/60 to about 60/40; or a mixture of water and ethanol in a volume ratio of from about 40/60 to about 60/40.

Regarding the process for preparing the hydroxyalkyl aminoimidazole compound, the subject invention provides that the process may be performed at a temperature of about 0° C. to about 100° C.

Regarding the process for preparing the hydroxyalkyl aminoimidazole compound, the subject invention provides that the process may be performed at a temperature of about 25° C. to about 70° C.

Regarding the process for preparing the hydroxyalkyl aminoimidazole compound, the subject invention provides that the process may be performed at a temperature of about 25° C. to about 50° C.

Regarding the process for preparing the hydroxyalkyl aminoimidazole compound, the subject invention provides that the process may be performed for a reaction time of from about 2 hours to about 72 hours. In general, the reaction time depends on the nature of the aldehyde; wherein the more hindered the aldehyde, the longer the reaction time.

The subject invention provides a bicyclic pyrrole compound having the structure

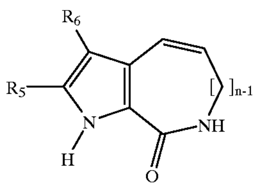

wherein n is an integer from 1 to about 6;

wherein $R_5$ and $R_6$ are the same or different, and are H; a $C_1$ to about $C_{10}$ straight chain alkyl group or branched alkyl group, which alkyl group is substituted or unsubstituted; or halogen.

The bicyclic pyrrole compound is useful as an intermediate in the preparation of hymenin, odiline, and analogues thereof, all useful as anti-microbial agents. The bicyclic pyrrole compound is also useful as an intermediate in the preparation of hymenialdinies and analogues thereof, which are useful as anti-cancer agents.

Regarding bicyclic pyrrole compound, the subject invention provides that the alkyl group may be substituted with halogen, alcohol, alkoxy, dialkyl amine, alkyl aryl amine, diaryl amine, thiol, or sulfide groups.

The subject invention provides the process for preparing the bicyclic pyrrole compound of the subject invention, wherein $R_5$, $R_6$, and n are the same as defined above, which process comprises:

reacting a pyrrole having the structure

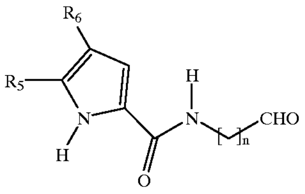

in a solvent, wherein the solvent is methane sulfonic acid, trifluoroacetic acid, or trifluoromethane sulfonic acid, to form the bicyclic pyrrole compound.

Regarding the process for preparing the bicyclic pyrrole compound, the subject invention provides that the process may be performed at a temperature of about 0° C. to about 100° C.

Regarding the process for preparing the bicyclic pyrrole compound, the subject invention provides that the process may be performed at a temperature of about 25° C. to about 100° C.

Regarding the process for preparing the bicyclic pyrrole compound, the subject invention provides that the process may be performed at a temperature of about 25° C. to about 50° C.

Regarding the process for preparing the bicyclic pyrrole compound, the subject invention provides that the process may be performed for a reaction time of from about 3 days to about 5 days. In general, the reaction time is solvent dependent; wherein when the solvent in methane sulfonic acid then the reaction time about 3 days; when the solvent is trifluoroacetic acid then the reaction time is about 5 days.

Regarding the process for preparing the bicyclic pyrrole compound, the subject invention provides that the solvent may be saturated with an inert gas. An example of an appropriate inert gas is argon. The inert gas is used to avoid oxidation of the pyrrole compound.

The subject invention provides a hymenin compound having the structure

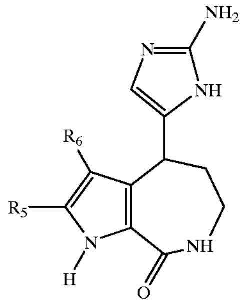

wherein $R_5$ and $R_6$ are the same or different, and are H; a $C_1$ to about $C_{10}$ straight chain alkyl group or branched alkyl group or branched alkyl group, which alkyl is substituted or unsubstituted; of F, Cl, or I.

The hymenin compound is useful as an anti-hypertensive and an intermediate in the preparation of analogues thereof, which are also useful as anti-hypertensive agents.

Regarding the hymenin compound of the subject invention, the subject invention provides that the alkyl groups may be substituted with halogen, alcohol, alkoxy, dialkyl amine, alkyl aryl amine, diaryl amine, thiol, or sulfide groups.

The subject invention provides the process for preparing the hymenin compound of the subject invention, wherein $R_5$ and $R_6$ are the same or different, and are H; a $C_1$ to about $C_{10}$ straight chain alkyl or branched alkyl, which alkyl may be substituted or unsubstituted; or halogen; which process comprises:

reacting one molecular equivalent of an aldehyde having the structure

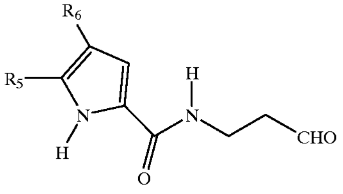

with one molecular equivalent of 2-aminoimidazole or a salt of 2-aminoimidazole; in a solvent wherein the solvent is methane sulfonic acid, trifluoroacetic acid, or trifluoromethane sulfonic acid; to form the hymenin compound.

Regarding the process for preparing the hymenin compound, the subject invention provides that the process may be performed at a temperature of about 0° C. to about 100° C. Regarding the process for preparing the hymenin compound, the subject invention provides that the process may be performed at a temperature of about 25° C. to about 50° C. Regarding the process for preparing the hymenin compound, the subject invention provides that the process may be performed at a temperature of about 30° C.

Regarding the process for preparing the hymenin compound, the subject invention provides that the process may be performed for a reaction time of from about 3 days to about 5 days.

Regarding the process for preparing the hymenin compound, the subject invention provides that the solvent may be saturated with an inert gas. An example of an appropriate inert gas is argon. The inert gas is used to avoid oxidation of the compounds that could be oxidized by air that might be present in the solution. The subject invention provides an aldehyde aminoimidazole compound having the structure

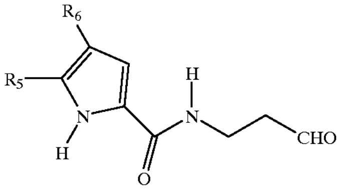

wherein $R_5$ and $R_6$ are the same or different, and are H; a $C_1$ to about $C_{10}$ straight chain alkyl group or branched alkyl group, which alkyl group is substituted or unsubstituted; or halogen.

The aldehyde aminoimidazole compound is useful as an intermediate in the preparation of the bicyclic pyrrole compound disclosed hereinabove and analogues thereof.

Regarding the aldehyde aminoimidazole compound of the subject invention, the subject invention provides that the alkyl groups may be substituted with halogen, alcohol, alkoxy, dialkyl amine, alkyl aryl amine, diaryl amine, thiol, or sulfide groups.

The subject invention provides the process for preparing the aldehyde aminoimidazole compound of the subject invention, wherein $R_5$ and $R_6$ are the same as defined for the aldehyde aminoimidazole compound; which process comprises:

reacting one molecular equivalent of a ketal having the structure

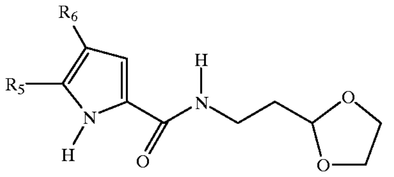

with 0.5 molecular equivalent of p-toluene sulfonic acid monohydrate, at a temperature of about 0° C. to about 100° C.;

in a solvent, wherein the solvent is a mixture of water and a polar nonhydroxylic organic solvent, and the volume ratio of the water and the polar nonhydroxylic organic solvent is from about 1/10 to about 10/1;

to form the aldehyde aminoimidazole compound.

Regarding the process for preparing the aldehyde aminoimidazole compound, the subject invention provides that the polar nonhydroxylic organic solvent may be N,N-dimethylformamide; dioxane; tetrahydrofuran; dimethyl sulfoxide; or acetonitrile.

Regarding the process for preparing the aldehyde aminoimidazole compound, and further regarding the volume ratio of the water and the polar nonhydroxylic organic solvent, the subject invention provides that the volume ratio of the water and the polar nonhydroxylic organic solvent may be from about 40/60 to about 60/40.

Regarding the process for preparing the aldehyde aminoimidazole compound, the subject invention provides that the solvent may be a mixture of water and acetone in a volume ratio of from about 40/60 to about 60/40.

Regarding the process for preparing the aldehyde aminoimidazole compound, the subject invention provides that the temperature may be about 80° C. to about 100° C.

Regarding the process for preparing the aldehyde aminoimidazole compound, the subject invention provides that the process may be performed for a reaction time of from about 3 hours to about 24 hours.

Regarding the process for preparing the aldehyde aminoimidazole compound, the subject invention provides that the process may be performed for a reaction time of from about 6 hours to about 10 hours.

The subject invention provides a ketal aminoimidazole compound having the structure

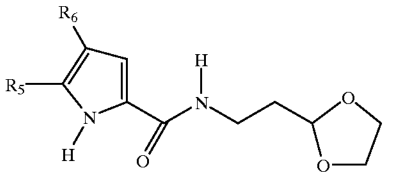

wherein $R_5$ and $R_6$ are the same or different, and are H; a $C_1$ to about $C_{10}$ straight chain alkyl group or branched alkyl group, which alkyl group is substituted or unsubstituted; or halogen.

The ketal aminoimidazole compound is useful as an intermediate in the preparation of the bicyclic pyrrole compound disclosed hereinabove and analogues thereof.

Regarding the ketal aminoimidazole compound of the subject invention, the subject invention provides that the alkyl group may be substituted with halogen, alcohol, alkoxy, dialkyl amine, alkyl aryl amine, diaryl amine, thiol, or sulfide groups.

The subject invention provides the process for preparing the ketal aminoimidazole compound of the subject invention, wherein $R_5$ and $R_6$ are the same as defined for the ketal aminoimidazole compound; which process comprises:

reacting one molecular equivalent of a trichloroacetylpyrrole having the structure

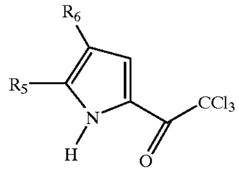

with one molecular equivalent of an aminoketal having structure

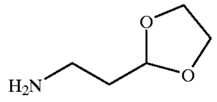

in a polar nonhydroxylic solvent, to form the ketal aminoimidazole compound.

Regarding the process for preparing the ketal aminoimidazole compound, the subject invention provides that the polar nonhydroxylic solvent may be N,N-dimethylformamide; dioxane; tetrahydrofuran; dimethyl sulfoxide; or acetonitrile.

Regarding the process for preparing the ketal aminoimidazole compound, the subject invention provides that the polar nonhydroxylic solvent is acetonitrile.

Regarding the process for preparing the ketal aminoimidazole compound, the subject invention provides that the process may be performed at a temperature of about 25° C. to about 70° C.

Regarding the process for preparing the ketal aminoimidazole compound, the subject invention provides that the process may be performed at a temperature of about 25° C. to about 50° C.

Regarding the process for preparing the ketal aminoimidazole compound, the subject invention provides that the process may be performed for a reaction time of from about 5 hours to about 48 hours.

Regarding the process for preparing the ketal aminoimidazole compound, the subject invention provides that the process may be performed for a reaction time of from about 16 hours to about 48 hours.

Regarding the process for preparing the ketal aminoimidazole compound, the subject invention provides that the polar nonhydroxylic solvent may be saturated with an inert gas. The inert gas is used to avoid oxidation of the compounds that could be oxidized by air that might be in the solution. An example of an appropriate inert gas is argon.

Regarding the process for preparing the ketal aminoimidazole compound, the subject invention provides that the polar nonhydroxlic solvent may additionally contain one equivalent of triethylamine. The triethylamine is used to neutralize acid that is formed in the process.

The subject invention provides a tricyclic compound having the structure

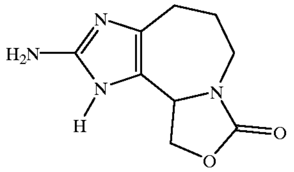

The tricyclic compound is useful as an anti-microbial compound. The tricyclic compound is also useful as an anti-cancer agent.

The subject invention provides the process for preparing the tricyclic compound of the subject invention, which process comprises:

reacting one molecular equivalent of 2-chloroethanal, with one molecular equivalent of a propylamine substituted aminoimidazole having the structure

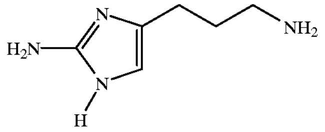

in a polar hydroxylic solvent or a polar nonhydroxylic solvent, to form the tricyclic compound.

Regarding the process for preparing the tricyclic compound, the subject invention provides that the polar hydroxylic solvent may be a mixture of water and an organic polar solvent, and the volume ratio of the water and the organic polar solvent is from about 1/10 to about 10/1.

Regarding the process for preparing the tricyclic compound, and further regarding the volume ratio of the water and the organic polar solvent, the subject invention provides that the volume ratio of the water and the organic polar solvent is from about 40/60 to about 60/40.

Regarding the process for preparing the tricyclic compound, and further regarding the organic polar solvent, the subject invention provides that the organic polar solvent may be methanol; ethanol; N,N-dimethylformamide; dioxane; tetrahydrofuran; dimethyl sulfoxide; or acetonitrile.

Regarding the process for preparing the tricyclic compound, the subject invention provides that the polar hydroxylic solvent may be a mixture of water and methanol in a volume ratio of from about 40/60 to about 60/40; or a mixture of water and ethanol in a volume ratio of from about 40/60 to about 60/40.

Regarding the process for preparing the tricyclic compound, the subject invention provides that the polar nonhydroxylic solvent may be N,N-dimethylformamide; dioxane; tetrahydrofuran; dimethyl sulfoxide; or acetonitrile.

Regarding the process for preparing the tricyclic compound, the subject invention provides that the process may be performed at a temperature of about 0° C. to about 100° C.

Regarding the process for preparing the tricyclic compound, the subject invention provides that the process may be performed at a temperature of about 0° C. to about 50° C.

Regarding the process for preparing the tricyclic compound, the subject invention provides that the process may be performed at a temperature of about 25° C.

Regarding the process for preparing the tricyclic compound, the subject invention provides that the process may be performed for a reaction time of from about 5 minutes to about 5 hours.

Regarding the process for preparing the tricyclic compound, the subject invention provides that the process may be performed for a reaction time of from about 1 hour to about 5 hours.

The subject invention provides a tetrahydropurine compound having the structure

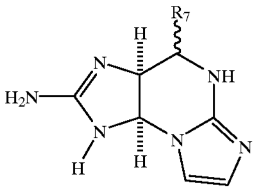

wherein $R_7$ is a $C_1$ to about $C_{10}$ alkyl group, which is a primary alkyl group, a secondary branched alkyl group, or a tertiary branched alkyl group wherein the tertiary carbon of the tertiary branched alkyl group is separated from the ring structure of the tetrahydropurine compound by at least one carbon atom, which alkyl groups are substituted or unsubstituted.

Regarding the tetrahydropurine compound of the subject invention, the subject invention provides that the alkyl groups may be substituted with halogen, alcohol, alkoxy, dialkyl amine, alkyl aryl amine, diaryl amine, thiol, or sulfide substituted groups. The tetrahydropurine compound and analogues thereof are active as sodium channel inhibitors. Consequently, the tetrahydropurine compound and analogues thereof are useful for treating various central nervous system disorders, including ischaemia, shock, Parkinson's disease and epilepsy.

The subject invention provides the process for preparing the tetrahydropurine compound of the subject invention, which process comprises:

is reacting one molecular equivalent of 2-aminoimidazole or a salt of 2-aminoimidazole, with one molecular equivalent of an aldehyde having the structure $R_7$—C(H)=0 in a polar hydroxylic solvent, to form the tetrahydropurine compound.

Regarding the process for preparing the tetrahydropurine compound, the subject invention provides that the polar hydroxylic solvent may be a mixture of water and an organic polar solvent, and the volume ratio of the water and the organic polar solvent is from about 1/10 to about 10/1.

Regarding the process for preparing the tetrahydropurine compound, and further regarding the volume ratio of the water and the organic polar solvent, the subject invention provides that the volume ratio of the water and the organic polar solvent is from about 40/60 to about 60/40.

Regarding the process for preparing the tetrahydropurine compound, and further regarding the organic polar solvent, the subject invention provides that the organic polar solvent may be methanol; ethanol; N,N-dimethylformamide; dioxane; tetrahydrofuran; dimethyl sulfoxide; or acetonitrile.

Regarding the process for preparing the tetrahydropurine compound, the subject invention provides that the polar hydroxylic solvent may be a mixture of water and methanol in a volume ratio of from about 40/60 to about 60/40; or a mixture of water and ethanol in a volume ratio of from about 40/60 to about 60/40.

Regarding the process for preparing the tetrahydropurine compound, the subject invention provides that the process may be performed at a temperature of about 0° C. to about 100° C.

Regarding the process for preparing the tetrahydropurine compound, the subject invention provides that the process may be performed at a temperature of about 25° C. to about 70° C.

Regarding the process for preparing the tetrahydropurine compound, the subject invention provides that the process may be performed at a temperature of about 25° C. to about 50° C.

Regarding the process for preparing the tetrahydropurine compound, the subject invention provides that the process may be performed for a reaction time of from about 2 hours to about 16 hours.

Regarding the process for preparing the tetrahydropurine compound, the subject invention provides that the process may be performed for a reaction time of from about 4 hours to about 16 hours.

The present invention therefore provides compounds for treating hypertension, cancer, central nervous system disorders and microbial infections. Treatment comprises administering each compound disclosed herein in an amount effective to treat hypertension, cancer, central nervous system disorders and microbial infections. The compounds provided herein may be constituted into any form suitable for the mode of administration selected. Compounds suitable for oral administration include solid forms, such as pills, capsules, granules, tablets, and powders, and liquid forms, such as solutions, syrups, elixers, and suspensions. Forms useful for parenteral administration include sterile solutions, emulsions, and suspensions.

The drug may otherwise be prepared as a sterile solid composition which may be dissolved or suspended at the time of administration using sterile water, saline, or other appropriate sterile injectible medium. Carriers are intended to include necessary and inert binders, suspending agents, lubricants, flavorants, sweeteners, preservatives, dyes, and coatings.

The total daily dose of the compounds disclosed herein administered to a human or other mammal in single or divided doses can be in amounts of, for example, from about 0.01 to about 50 mg/kg of body weight, or more typically from about 0.2 to about 30 mg/kg of body weight. Optimal dosages to be administered may be determined by those skilled in the art, and will vary with the particular compound in use, the strength of the preparation, the mode of administration, and the advancement of the disease condition. Additional factors depending on the particular patient being treated will result in a need to adjust dosages, including patient age, weight, gender, diet, and time of administration.

Experimental Details

Chemical reagents are obtained at various chemical supply companies, such as Fisher, Pittsburgh, Pa; Aldrich Chemical Company, Milwaukee, Wis.; and Spectrum Chemical Company, New Brunswick, N.J.

Experiment One

A common structural unit encountered in biologically active marine alkaloids is the 2-aminoimidazole nucleus. (For reviews of marine alkaloids, see ref. 1, 2, 3, 4; for recent reports of biologically active aminoimidazole derivatives, see ref. 5, 6, 7, 8, 9, 10, 11, 12). This weakly basic heterocycle is also an integral component of the highly fluorescent marine pigments known collectively as zoanthoxanthins (ref. 13, 14, 15, 16, 17, 18, 19, 20, 21, 22). The structurally related linear zoanthoxanthins (1) and angular pseudozoanthoxanthins (2) are representative of the zoanthoxanthin family in which over twenty N-methylated variations exist. The ring system of these pigments is based on either a 1,3,5,7-tetrazacyclopent[f]azulene (1) or a 1,3,7,9-tetrazacyclopent[e]azulene (2) skeleton. The latter occurs in two types depending on the N-methylation pattern. Several of these metabolites have been assayed for biological activity. They include the DNA intercalators zoanthoxanthin (1B) and 3-norzoanthoxanthin (1C) both of which inhibit the activity of rat liver DNA polymerase in vitro (ref. 23, 24), while paragracine (2B) possesses papaverine-like and antihistamine properties as well as having sodium channel blocking effects (ref. 21, 22). The biosynthesis of zoanthoxanthins has not been determined and awaits experimental verification. A longstanding hypothesis by Prota (ref. 15), however, involves the dimerization of two $C_5N_3$ monomers thought to be derived from arginine. Although the exact nature of the $C_5N_3$ monomer remains unknown, it is unclear how this moiety would result from arginine metabolism. In this report, we describe the conversions of an arginine derived $C_3N_3$ heterocycle, namely 2-aminoimidazole (AI), into both parazoanthoxanthin A (1A) and pseudozoanthoxanthin A (2A) thus implicating the intermediacy of 2-aminoimidazole as an in vivo progenitor of zoanthoxanthins.

AI

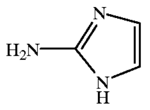

(1)

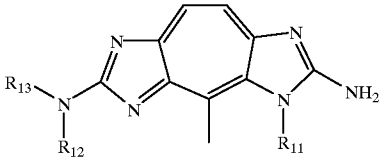

(2)

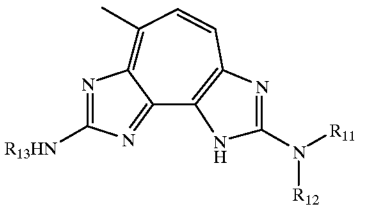

a: $R_{11} = R_{12} = R_{13} = H$
b: $R_{11} = R_{12} = R_{13} = CH_3$
c: $R_{11} = H$, $R_{12} = R_{13} = CH3$

The notion that zoanthoxanthins (1) and (2) could possibly be derived from 2-aminoimidazole (AI) is based on the identification of (AI) as a marine metabolite of the sponge *Reneira cratera* (ref. 25). Combination of four molecules of the $C_3N_3$ heterocycle with loss of two molecules of guanidine would give the desired $C_{10}N_6$ pigments. (For acid promoted dimerizations and trimerizations of indoles and pyrroles, see ref. 26, 27). When 2-aminoimidazole sulfate was exposed to methanesulfonic acid at 23° C., no reaction occurred. Upon heating, however, between 140–150° C. for 20 hours, small amounts of parazoanthoxanthin A (1A) and pseudozoanthoxanthin A (2A) were obtained (10% yield) in a 4:1 ratio, respectfully. $^1$H NMR, UV, IR, and MS data are in agreement with previously reported values (ref. 15, 28, 29). Although no intermediates of the reaction have been confirmed, a possible mechanism for the formation of (1A) and (2A) is shown in Scheme (1) and is based on related chemistry observed for indoles and pyrroles. (For acid promoted dimerizations and trimerizations of indoles and pyrroles, see ref. 26, 27). Using sulfuric acid in place of methanesulfonic acid no zoanthoxanthins could be detected. The major product of the reaction is glycocyamidine (11) (ref. 30) which results from sulfonation of the starting material followed by hydrolysis. These results indicate that while involvement of (AI) in the biogenesis of zoanthoxanthins remains a curious possibility, its sole participation is unlikely.

(41% yield) and pseudozoanthoxanthin A (2A) (7% yield) were obtained. Most importantly, moderate amounts of (1A) and (2A) were produced at room temperature after 7 days. Under acidic conditions, the proton serves as a natural protecting group for nitrogen as well as catalyst for hydroxyalkylation and subsequent dimerization. Similar results were seen with pyruvic acid and the more highly reduced two-carbon unit, acetaldehyde, but with less efficiency. Reactions

SCHEME (1)

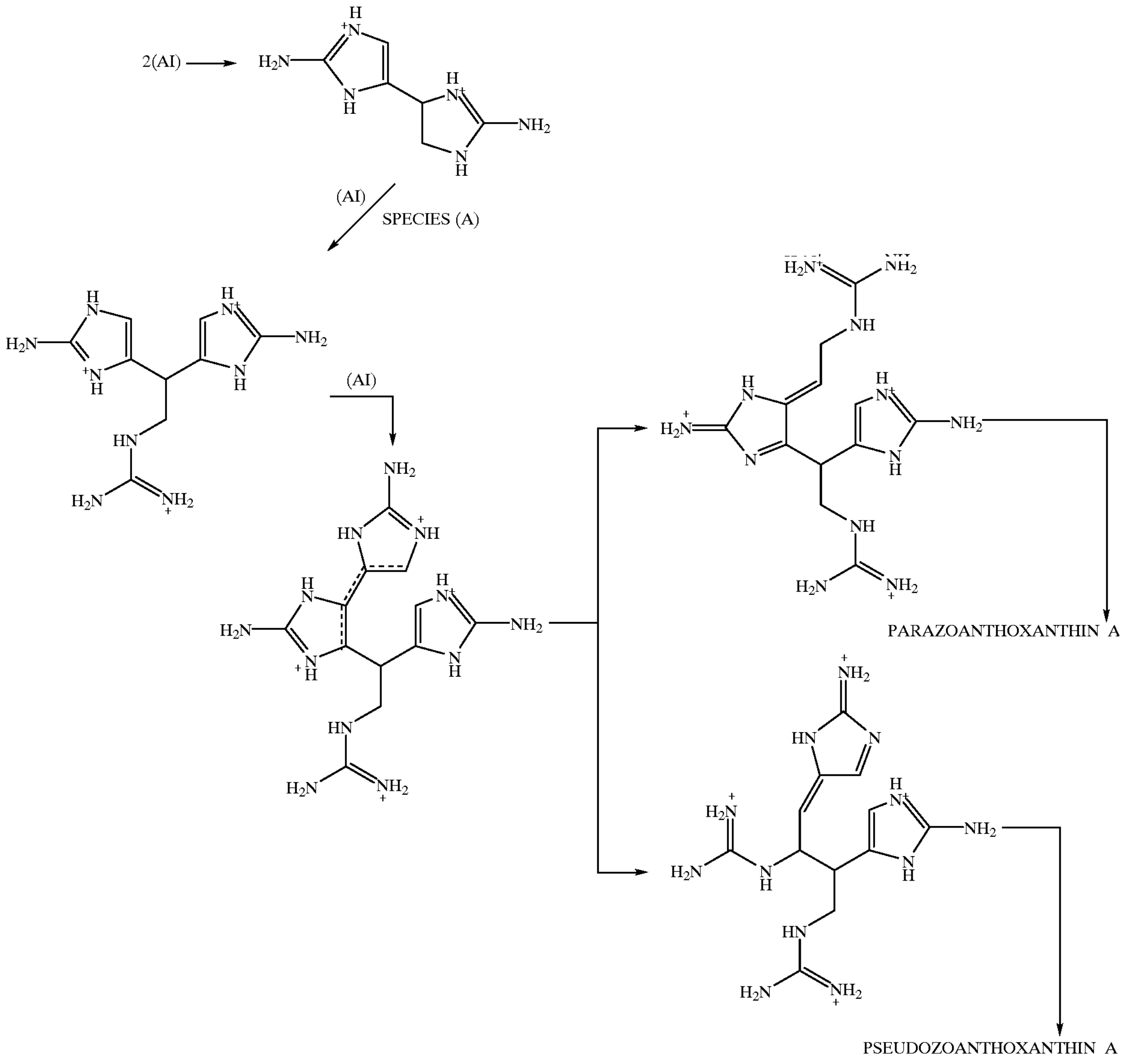

Nature's utilization of a potential counterpart in the formation of zoanthoxanthins forms a basis of our biogenic hypothesis and involves the introduction of a two-carbon unit (or equivalent) to the $C_3N_3$ heterocycle as the penultimate step prior to dimerization. Incorporation of this hypothetical two-carbon entity could be accomplished by a hitherto unknown hydroxyalkylation of 2-aminoimidazole with a suitably functionalized two-carbon aldehyde or pyruvic acid. To test this hypothesis, 2-aminoimidazole sulfate was heated at 95–100° C. with chloroacetaldehyde in concentrated hydrochloric acid for 24 hours. After basification to pH 12 and chromatography, parazoanthoxanthin A (1A)

involving pyruvic acid and acetaldehyde were carried out in 37% HCl between 95–100° C. for 24 hours. Acetaldehyde gave a 25% yield of parazoanthoxanthin A and pseudozoanthoxanthin A in a 3:1 ratio, respectively, whereas pyruvic acid produced a 15% yield of parazoanthoxanthin A and trace amounts of pseudozoanthoxanthin A. With these reactants, decarboxylation and/or final oxidation to the ten-electron azulene ring system is necessary (the oxidation is probably assisted by sulfuric acid derived from the commercial starting material, 2-aminoimidazole sulfate) and most likely accounts for the lower overall yields. At 23° C., the reaction between (AI) and acetaldehyde afforded products (12) (ref. 29); and (14) [Compound 5.2HCl, colorless solid, mp 240° C. (dec); $^1$H NMR (DMSO-$D_6$, 300 MHz) δ ppm: 1.51 (d, 7.2 Hz, 3H), 3.97 (q, 7.2 Hz, 1H), 6.65 (s, 2H), 7.37 (s, 4H, exchanged with $D_2O$), 11.85 (s, 2H, exchanged with $D_2O$), 12.37 (s, 2H, exchanged with $D_2O$); $^{13}$C NMR (free-base, DMSO-$D_6$, 75.1 MHz) δ ppm: 20.0 (q), 30.4 (d), 111.0 (d), 135.8 (s), 148.9 (s); IR (nujol) υ $cm^{-1}$: 3240, 3126, 1667; MS (CI, $NH_3$) m/z 193 ($MH^+$)] (10–40% yields); in addition to small amounts of zoanthoxanthins. Formation of (14) [Dimer (14), when heated at 95–100° C. with 1 eq. of acetaldehyde produced parazoanthoxanthin A], a precursor to parazoanthoxanthin A (1A), can be explained by dehydration of (12) to intermediate (B) followed by C-attack of the imidazole to the exocyclic double bond. Intermediate (14) could next undergo hydroxyalkylation with acetaldehyde followed by dehydration, cyclization, and oxidation to give (1A). A similar process in which initial addition to the endocyclic double bond of species (B) would account for the formation of pseudozoanthoxanthin A (2A), although no intermediates have been isolated. Whether the actual biosynthetic pathway proceeds via a sequential series of hydroxyalkylation-dimerization-hydroxyalkylation events involving 2-aminoimidazole or by direct dimerization of two $C_5N_3$ monomers (ref. 28, 29) remains to be determined. Our results in combination with the known metabolic conversion of arginine to (AI) (ref. 31) suggest that the key biosynthetic intermediate is not a direct product of arginine metabolism but evolves from hydroxyalkylation of arginine derived (AI). One additional consideration is formation of the methylated metabolites of zoanthoxanthins since they comprise the majority of pigments isolated. The parent compounds (1A) and (2A) could serve as potential precursors in a late methylation scheme, or contrastly, an early, predimeric methylation process would yield N-methylated 2-aminoimidazoles as biogenic forerunners.

(11)

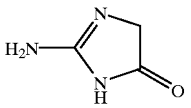

(12)

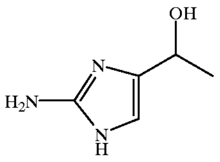

(14)

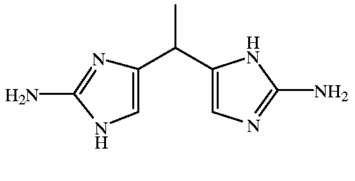

(B)

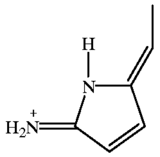

The generality and simplicity of hydroxyalkylation should find useful applications in the synthesis of aminoimidazole heterocycles. In our initial demonstration, we have shown that zoanthoxanthins can be prepared in (essentially) a single step from commercially available 2-aminoimidazole sulfate and acetaldehydes. The mild reaction conditions under which pigments (1A) and (2A) are produced suggests that the series of events leading to their formation parallel those operating in nature. Due to the difficulties encountered in culturing marine organisms, biosynthetic studies in the area of marine alkaloids are rare. The biogenic chemistry developed here, points to 2-aminoimidazole as a potential precursor to zoanthoxanthins.

Other references of interest are ref. 68, 69, 70.

Experiment Two

A. Specific Aims

The development of new synthetic methodologies and strategies for the construction of guanidine-based marine natural products possessing important biological functions is considered. The generality of this approach is demonstrated by the synthesis of zoanthoxanthins (1) and (2), hymenin (3), hymenialdisines (4), sceptrin (5), oxysceptrin (6), ageliferins (7), girolline (8), as well as saxitoxin (9). Collectively, these and other structurally related compounds possess potent biological activities. They include antiviral, antileukemic, antineoplastic, antiserotonergic as well as α-adrenoceptor and ion-channel blocking properties. In addition, a rare example of ATPase stimulating activities of myosin and actomyosin has recently been observed. Although many of these marine metabolites are structurally unique, they appear, however, to diverge from a common biogenetically related intermediate. Possible biosynthetic pathways for the in vivo formation of these marine metabolites are considered. The development of methods for transforming 2-aminoimidazole (AI) into key intermediates for the synthesis of the naturally occurring compounds is considered.

B. Background and Significance

Nitrogen-containing marine natural products (ref. 1, 2, 3, 32) are often unique to marine organisms having structural features that are not encountered in terrestrial flora or fauna. Many of these metabolites are non-traditional guanidine-based alkaloids that possess powerful biological activities. A common structural unit contained in many of these alkaloids is the 2-aminoimidazole (AI) moiety. This weakly basic heterocycle and its functionalized derivatives are present in over fifty marine alkaloids isolated to date. In fact, 2-aminoimidazole (AI) itself is a marine metabolite that has been obtained from the sponge *Reneira crotera* (ref. 25). It has also been shown to result from arginine metabolism in streptomyces eurocidius (ref. 31). The following representative examples, together with a brief description of their biological activities, serve to illustrate the ubiquitous nature of the 2-aminoimidazole moiety contained in marine alkaloids.

Zoanthoxanthins (1) and (2)

One family of colonial anthozoans of the order Zoanthidea yields a variety of yellow, highly fluorescent pigments known collectively as zoanthoxanthins (ref. 13, 14, 15, 16, 17, 18, 19, 20, 21, 22). These pigments are responsible for the bright yellow pigmentation of numerous zoanthids of the genus Parazoanthus. Structurally, zoanthoxanthins can be grouped into two distinct classes, linear zoanthoxanthins (1,3,5,7-tetrazacyclopent[f]azulenes) (1) and angular pseudozoanthoxanthins (1, 3, 7, 9-tetrazacyclopent[e]azulenes) (2). Within these two groups over twenty variations of these metabolites are known and can be distinguished mainly by their N-methylation patterns. The synthesis of parazoanthoxanthin A (1) ($R_{11}$=$R_{12}$=$R_{13}$=H), and pseudozoanthoxanthin (2)

($R_{11}$=R$1_2$=$R_{13}$=H), has been achieved from 2-amino-4-α or β-hydroxyethylimidazoles prepared in several steps (ref. 28, 29).

The biological significance and pharmacological properties of these metabolites remain virtually unknown. Of the few known biological activities of zoanthoxanthins, paragracine (2) ($R_{11}$=$R_{12}$=$R_{13}$=$CH_3$), has been shown to have papaverine-like and antihistamine properties (ref. 21, 22) while zoanthoxanthin (1) ($R_{11}$=$R_{12}$=$R_{13}$=$CH_3$), and 3-norzoanthoxanthin (1) ($R_{11}$=H, $R_{12}$=$R_{13}$=$CH_3$), have been shown to inhibit rat liver DNA polymerase in vitro. The role of inhibition is presumably through intercalative-type binding to duplex DNA (ref. 23, 24).

AI

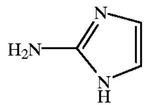

(1)

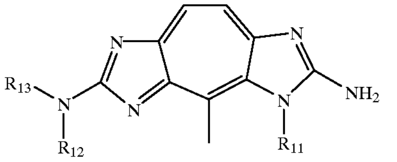

(2)

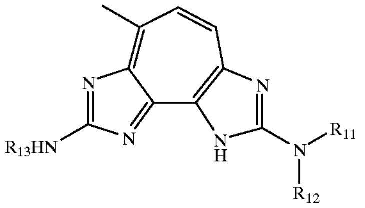

a: $R_{11}$ = $R_{12}$ = $R_{13}$ = H
b: $R_{11}$ = $R_{12}$ = $R_{13}$ = $CH_3$
c: $R_{11}$ = H, $R_{12}$ = $R_{13}$ = CH3

Hymenin (3) and Hymenialdisines (4)

Hymenin (3) (ref. 6, 33) has been identified as the active constituent of the sponge Hymenacidon sp. possessing potent α-adrenoceptor blocking activity. At 5 mg/kg, hymenin produced a 15±1 mm Hg reduction in arterial blood pressure in rats and its hypotensive effects lasted at least thirty minutes. In addition, hymenin at micromolar concentrations in isolated rabbit aorta caused a parallel rightward shift of the dose-response curve for norepinephrine (NE) without affecting responses for histamine or KCl. These results suggest specific competitive antagonism of NE binding to its receptor. Hymenin represents one member of fused pyrrole-seven-membered ring lactams containing a 2-aminoimidazole appendage. The structurally related metabolite, yellow compound (debromohymenialdisine) (4) (R=H) and hymenialdisine (4) (R=Br) have also been isolated from marine sources (ref. 34, 35, 36, 37). Hymenialdisines exhibited cytostatic and antineoplastic activities against murine P388 lymphocytic leukemic ($ED_{50}$ 2.5 mg/ml and T/C 143 @ 3.6 mg/kg) (ref. 8).

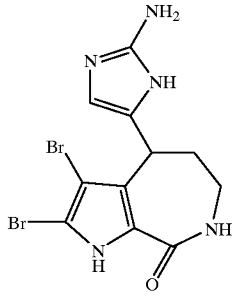

(3) HYMENIN

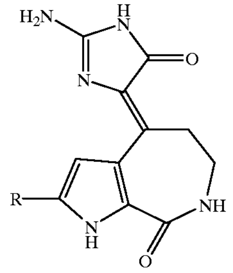

(4) R = H OR Br
HYMENIALDISINES

DEBROMOHYMENIALDISINE (R = H)
HYMENIALDISINE (R = Br)

Sceptrin (5), Oxysceptrin (6), and Ageliferins (7)

Sceptrin (5) has been isolated from the marine sponge Agelas sp. (ref. 38). More recently, the isolation and structural determination of the closely related oxysceptrin (6) (ref. 39, 10) and ageliferins (7) (ref. 40, 9) have been reported. The unique structural feature of sceptrins is the cyclobutane ring system which is only sparsely seen in natural products. Both sceptrins and ageliferins are potent actomyosin ATPase activators (ref. 10, 9). The ATPase activity of myofibrils from rabbit skeletal muscle was elevated 150% of the control value at $10^{-5}$ M concentrations of these alkaloids. Since substances that moderate ATPase activities of myosin and actomyosin are rare, these alkaloids are invaluable chemical tools for investigating the mechanism of actinmyosin contractile systems.

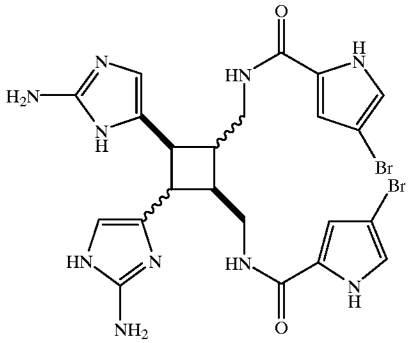

(5) SCEPTRIN

-continued

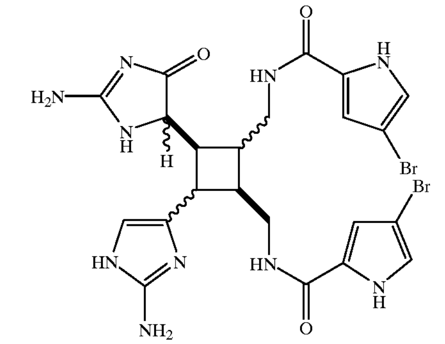

(6) OXYSCEPTRIN

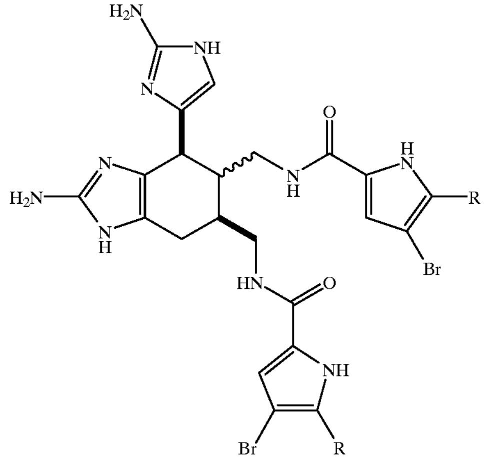

(7) AGELIFERINS

R = H OR Br

Girolline (8)

Girolline (8) (ref. 41) is a new antitumor agent isolated from the New Caledonian sponge *Pseudaxinissa cantharella.* This compound exhibited potent antitumor activities against P388 leukemic cells at concentrations as low as 1 ng/ml in vitro and at 1 mg/kg in vivo when administered intraperitoneally. This base has been recently prepared from imidazole carboxaldehyde in which the 2-amino group was introduced in the final step of the synthesis (ref. 42, 43, 11).

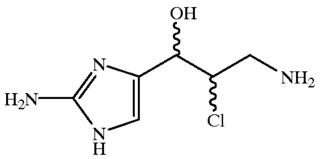

(8) GIROLLINE

Saxitoxin (9)

One of the most notable of marine toxins is saxitoxin (9) (ref. 44, 45, 46). This modified purine alkaloid has been responsible for numerous deaths resulting from paralytic shellfish poisoning. Saxitoxin is present in dinoflagellates and accumulates in shellfish or other sea fish via the food chain. The biological mode of action of saxitoxin is specific blockage of the sodium channel thus preventing passage of sodium ions across the cell membrane. Since its discovery, saxitoxin has proved to be an invaluable neurobiological tool for the study of ion channels. The lack of useful synthetic procedures (ref. 47, 48) for the synthesis of saxitoxin and suitably labeled analogues have prevented further advances in understanding structure and conformation as it relates to function.

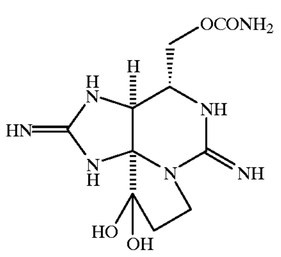

(9) SAXITOXIN

The chemistry of 2-aminoimidazoles is virtually undetermined. Many marine natural products contain this heterocyclic moiety. Some representative members of this alkaloid class with known biological activities are discussed here. There are, however, many natural derivatives which appear to be biogenetically related having diverged from a common, yet unidentified, intermediate. Further discussion involving biogenic hypotheses of these metabolites is described later. Since the majority of these marine products have been isolated from depths ranging from 30 to 800 meters below sea level, metabolite availability has been a problem for both chemical and biochemical investigations. Very often, minute amounts contained within the marine source make it impractical to obtain suitable quantities of material necessary for further study.

C. Preliminary Studies

Preliminary investigations dealing with the chemistry of 2-aminoimidazole indicate we have made a breakthrough discovery which is outlined below.

Biogenic Implication of 2-Aminoimidazole from the Synthesis of Zoanthoxanthins

One step in the biogenesis of zoanthoxanthins has been postulated to involve dimerization of two $C_5N_3$ units derived from arginine (ref. 15). Although the exact nature of the $C_5N_3$ unit remains unknown, it is unlikely that this unit is a direct product of arginine metabolism. Since 2-aminoimidazole has been identified as a marine metabolite (ref. 25), our initial investigations entertained the possibility that zoanthoxanthins could be derived from four molecules of a $C_3N_3$ heterocycle with loss of two molecules of guanidine. The synthetic strategy is based on the acid promoted dimerization of pyrroles and indoles (ref. 26, 27). Treatment of tryptophan methylester with methanesulfonic acid at room temperature produces good yields of the hemisaturated C-2 dimer (10). Under similar conditions 2-aminoimidazole was virtually unreactive. However, when 2-aminoimidazole was heated in methanesulfonic acid between 140–150° C. for 20 hours, small amounts of parazoanthoxanthin A (1) and pseudozoanthoxanthin (2) were obtained in a 5:1 ratio, respectively. $^1$H NMR, UV, IR, and MS data were in agreement with previously reported values (ref. 15, 28, 29). The majority of the material recovered from the reaction was unreacted starting material. Although no intermediates of the reaction have yet been confirmed, a likely mechanism would involve an acid promoted dimerization of 2-aminoimidazole to Species (A) of Scheme (1) as the initial step. Scheme (1) shows the proposed mechanism for the formation of parazoanthoxanthin A and pseudozoanthoxanthin from 2-aminoimidazole (AI). When sulfuric acid was used in place of methanesulfonic acid, no zoanthoxanthins could be detected. The major product of the reaction is glycocyamidine (11) (ref. 30) which results from sulfonation of the starting material followed by hydrolysis.
(1)
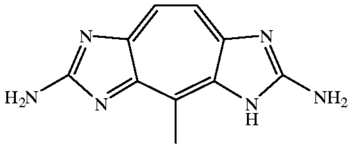
(2)
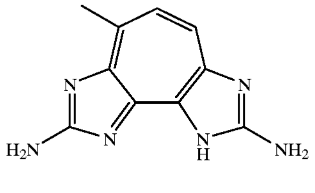
-continued
(10)
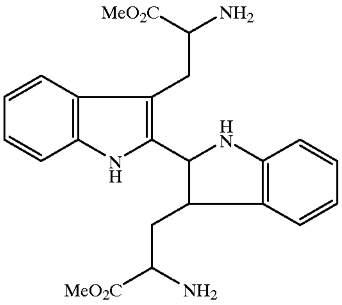
(11)
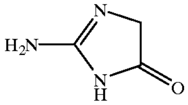
SCHEME (1)
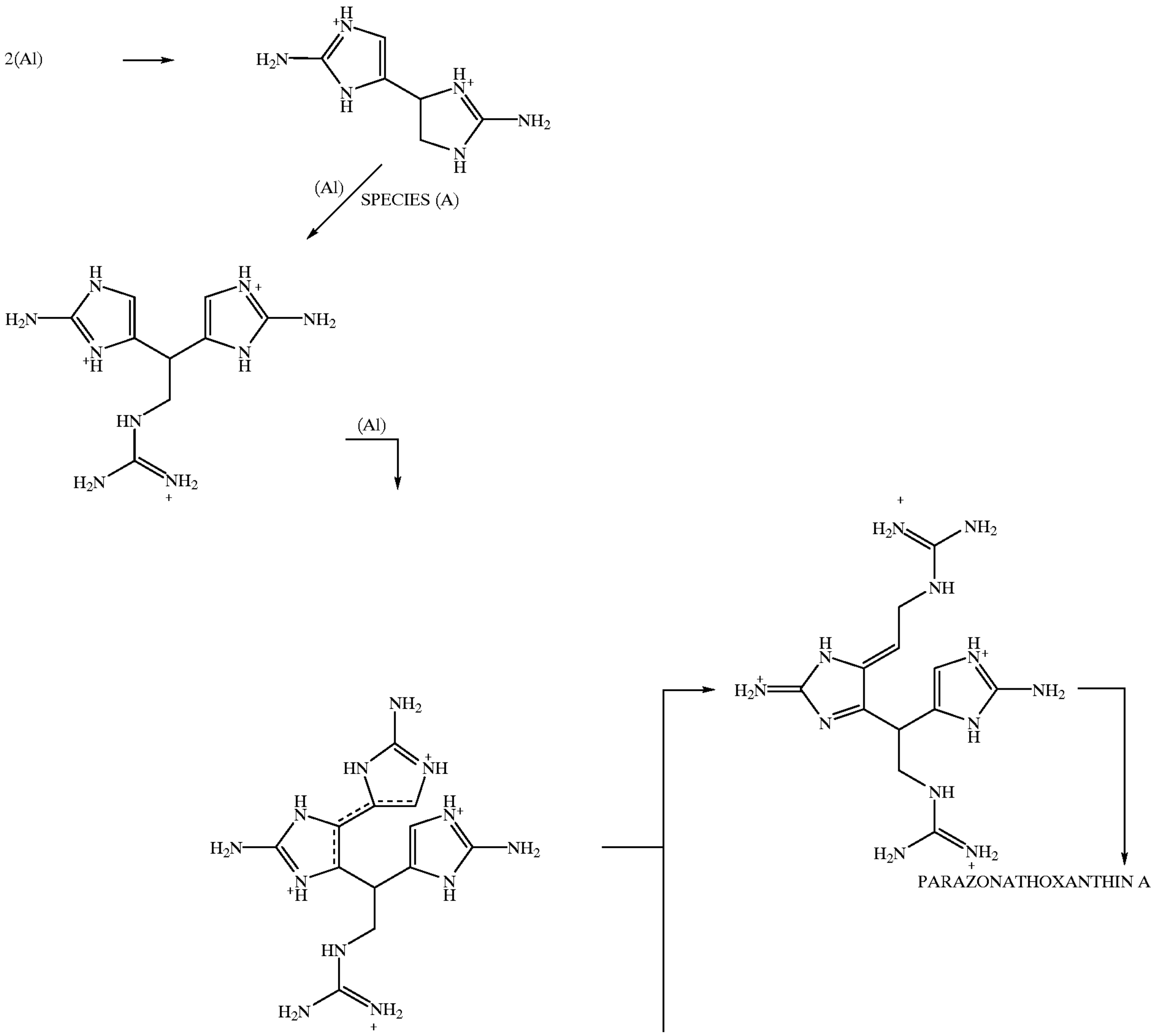

-continued

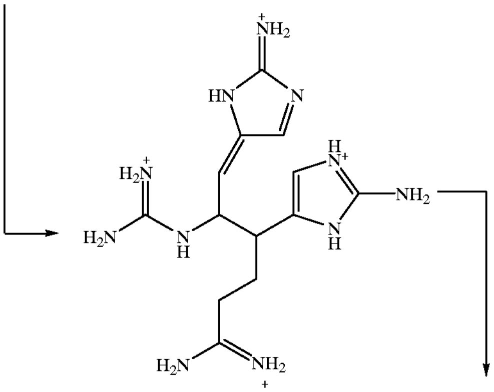

PSEUDOZANTHOXANTHIN A

These initial results indicate that while involvement of 2-aminoimidazole in the biogenesis of zoanthoxanthins remains an intriguing possibility, its sole participation is unlikely. One other consideration involves the introduction of a two-carbon unit to the $C_3N_3$ moiety as the penultimate biogenetic step prior to dimerization. Indeed, when 2-aminoimidazole was heated with chloroacetaldehyde in concentrated hydrochloric acid a 50% yield of zoanthoxanthins was obtained. The major product of the reaction is parazoanthoxanthin A (1). Similar results were seen with acetaldehyde but with lower overall yields. In this case, postdimeric oxidation to the ten electron azulene ring system is needed and is probably assisted by sulfuric acid derived from the commercial starting material, 2-aminoimidazole sulfate.

When acetaldehyde and 2-aminoimidazole were mixed under acidic aqueous conditions at 23° C., the following products (12), (13), (14), and (15), in addition to the aforementioned zoanthoxanthins, were obtained. These products can be explained by hydroxyalkylation of 2-aminoimidazole with acetaldehyde to give the $C_5N_3$ hydroxyethyl derivative (s). These results can be compared to that of imidazole in which no reaction is observed under analogous conditions. Dehydration of (12) to the diazafulvene intermediate (B), followed by N-attach or C-attack would produce the dimers (14) and (15). Under acidic conditions N—C dimer (15) undergoes conversion to the C—C dimer (14). While the possibility that zoanthoxanthins result from a concerted [4+6] cycloaddition involving intermediates (B) and (C) cannot be excluded (ref. 28, 29), the presence of dimer (14) strongly suggests a stepwise mechanism, Scheme (2). Scheme (2) shows the proposed mechanism for formation of parazoanthoxanthin A and pseudozoanthoxanthin from 2-aminoimidazole and acetaldehyde. In one of our most significant findings, small amounts of zoanthoxanthins were produced from 2-aminoimidazole and acetaldehyde at room temperature after 24 hours.

This result suggests that the biogenesis of zoanthoxanthins might involve the following series of events: (i) metabolism of arginine to 2-aminoimidazole (ref. 31); (ii) introduction of a two carbon unit by hydroxyalkylation; (iii) acid promoted dimerization, and, if necessary; (iv) oxidation to the azulene skeleton. The latter would depend upon the oxidation state of the two-carbon unit incorporated.

(12)

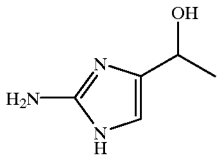

(13)

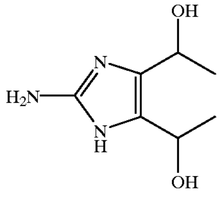

(14)

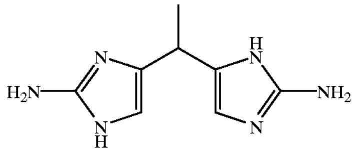

(15)

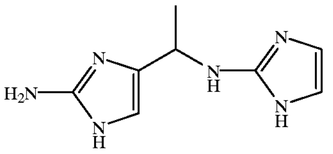

(B)

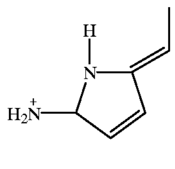

(C)

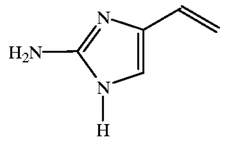

SCHEME (2)

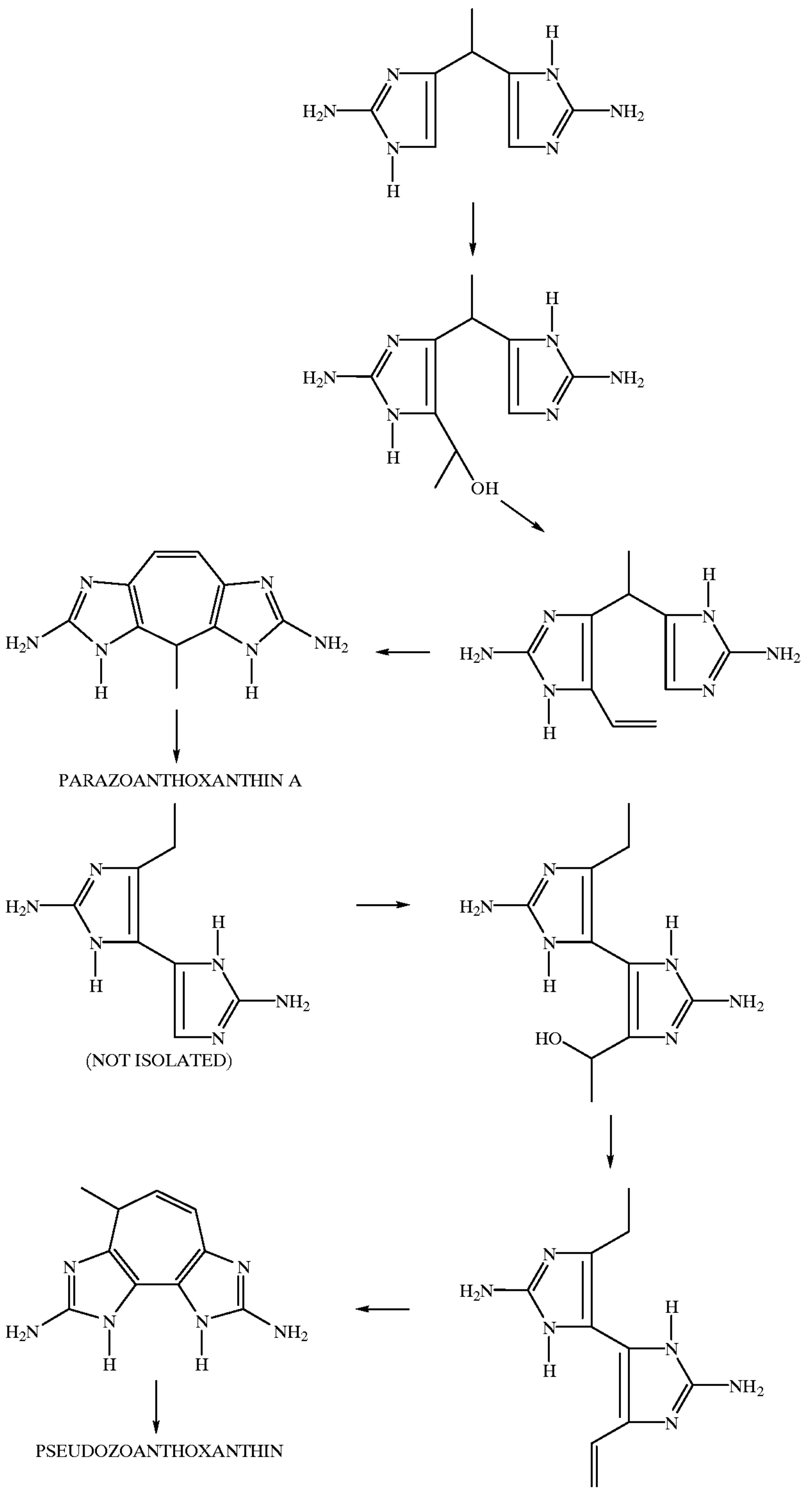

PARAZOANTHOXANTHIN A (NOT ISOLATED)

PSEUDOZOANTHOXANTHIN

A common feature unique to marine natural products is the frequent occurrence of halogenated and particularly brominated metabolites (ref. 49). Biosynthetically, introduction of bromine is believed to proceed via an active bromonium ion species generated from bromide and catalyzed bromoperoxidases (ref. 50). The interaction between bromonium ion and 2-aminoimidazoles is likely to be important. Many of the metabolites outlined here either contain bromine or may result from bromonium ion assisted oxidations/transformations. In order to delineate the bromination chemistry of 2-aminoimidazoles, the following transformations have been accomplished, Scheme (3). Scheme (3) shows the reactions of 2-aminoimidazoles with bromine. In contrast to the bromination of imidazoles (ref. 51, 52, 53), which does not occur under acidic conditions, the 2-amino analogue readily reacts with bromine in concentrated HCl or $H_2SO_4$. Under these conditions, incorporation of bromine was not observed in the final product. Moreover, oxidation of 4-ethylaminoimidazole [ref. 54 (preparation for 2-amino-4-ethylimidazole); 55] with bromine produced parazoanthoxanthin A (1) and pseudozoanthoxanthin (2) in moderate yield. When the reaction was carried out in sulfuric acid at 23° C., a 30% yield of the dimer (22) was obtained. These results further manifest a stepwise process for the formation of zoanthoxanthins.

By developing the chemistry of 2-aminoimidazole, several important findings have been made. In general, we have discovered a method that allows introduction of alkyl sidechains to the 4,(5)-carbon of 2-aminoimidazole. The reaction appears general and involves a simple hydroxyalkylation of 2-aminoimidazole with the requisite aldehyde. This results in the formation of a new carbon-carbon bond. In particular, we have initially applied this methodology by demonstrating that zoanthoxanthins can be synthesized in a single step from commercially available 2-aminoimidazole sulfate and acetaldehydes. The mild reaction conditions under which these natural metabolites are formed suggest that the series of steps leading to these products parallel those found in nature. Due to the difficulties involved in culturing marine organisms, biosynthetic studies in the area of marine alkaloids are extremely rare. The biogenic chemistry developed here points to 2-aminoimidazole as a natural precursor to zoanthoxanthins.

SCHEME (3)

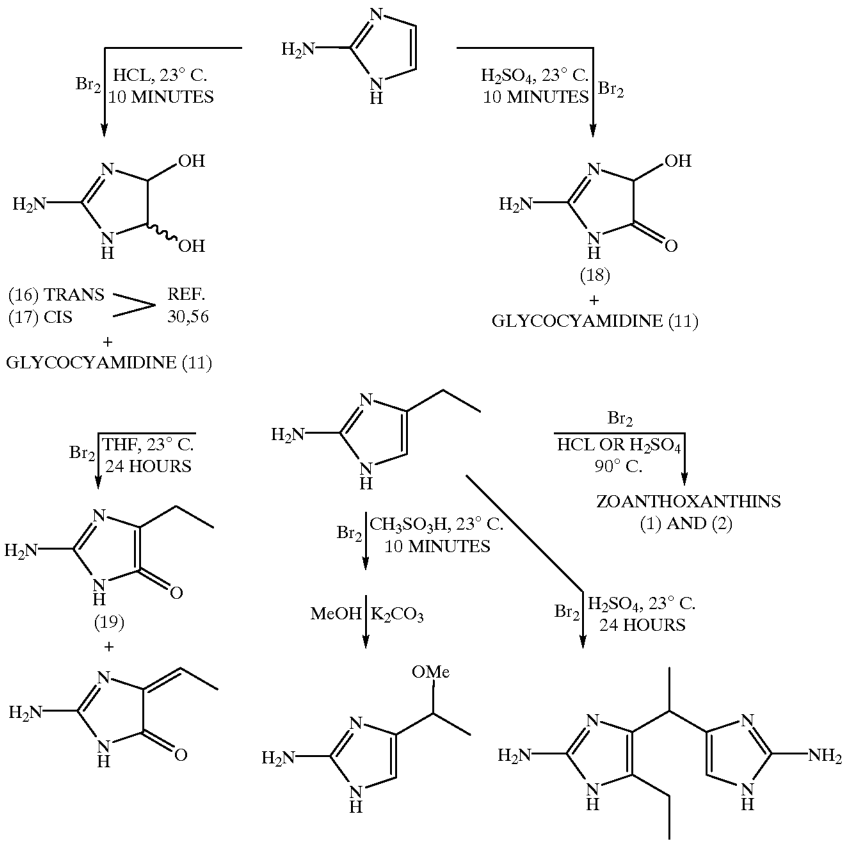

(20) (21) (22)

D. Methods

The basic elements entail coupling of 2-aminoimidazole with the requisite aldehyde and its ensuing transformation to the natural product. The hydroxyalkyl aminoimidazole constitutes a versatile intermediate, since it can be potentially converted to a wide variety of different marine alkaloid ring systems. This approach is likely biomimetic, and necessarily convergent for efficiency while potentially divergent for versatility. The general outline of this strategy is depicted below.

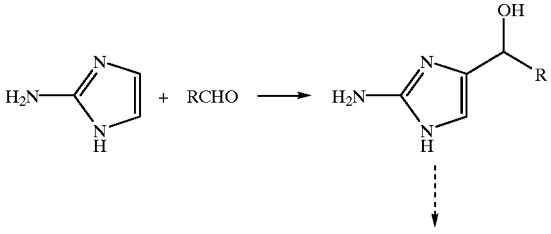

AMINOIMIDAZOLE MARINE NATURAL PRODUCTS

The constitution of the novel fused seven-membered ring lactams of the hymenin family is designed to test a likely biosynthetic pathway. The reactions are simple to carry out and are based on the aminoimidazole chemistry described in Section C. Formation of 2-amino-α-hydroxyalkyl imidazoles from 2-aminoimidazole and the corresponding aldehydes proceeds efficiently at 23° C. in neutral or acidic media. The resulting α-hydroxyalkyl aminoimidazole can be activated by acid or base catalysis to form, presumably, a reactive diazafulvene intermediate. In presence of nucleophiles, addition can occur at the α-position of the alkyl side chain. In the present case, R would be derived from a 3-carbon aldehyde linked to an amide pyrrole, Scheme (4). Scheme (4) shows the synthesis of hymenin (3), phakellin (27) and (28), and oroidin (29) marine alkaloids. This 3-carbon unit should be easily prepared from 3-aminopropanol and the trichloroacetylpyrrole (ref. 57, 58, 59). Condensation and oxidation of the resulting alcohol would give the desired aldehyde (24) of Scheme (4). By analogy with the hydroxyalkylation chemistry for the synthesis of zoanthoxanthins, aldehyde (24) would undergo facile transformation with 2-aminoimidazole giving the hydroxyalkyl derivative (25), Scheme (4). Dehydration of alcohol (25) under acidic conditions generates the active resonance stabilized intermediate (D), Scheme (4). In contrast to the intermolecular dimerization of intermediates seen in the zoanthoxanthin synthesis, the intermediate (D) possesses several nucleophilic groups that could intramolecularly add to the α-carbon. Attack at this position by the pyrrole carbon would give (±)-hymenin (3). Although the possible nucleophilic participation of the amide oxygen is anticipated, the resulting isoxazoline species (E), Scheme (4), would most likely be in equilibrium with species (D) in acidic media. This equilibration should facilitate formation of the 7-membered lactam ring system of (±)-hymenin (3).

SCHEME (4)

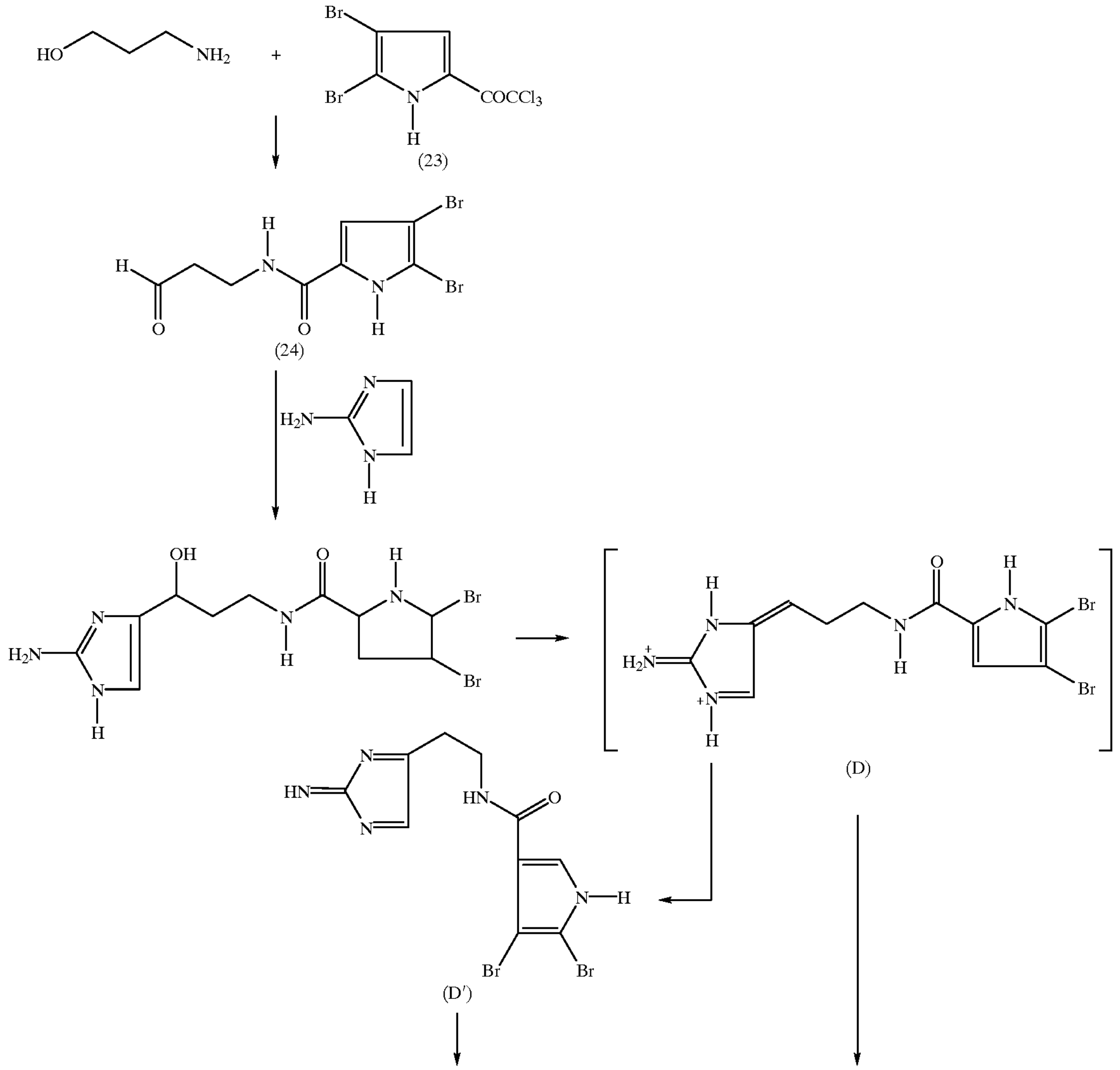

(23)

(24)

(D)

(D')

-continued

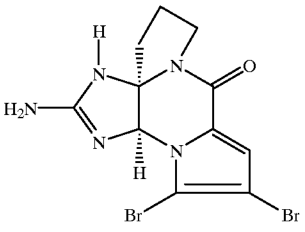

(27)

AND

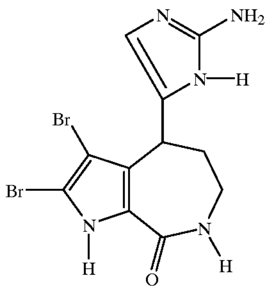

(3) HYMENIN

AND

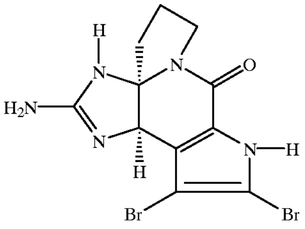

(28)

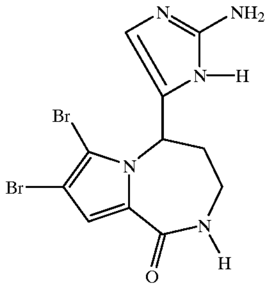

(26)

(25)

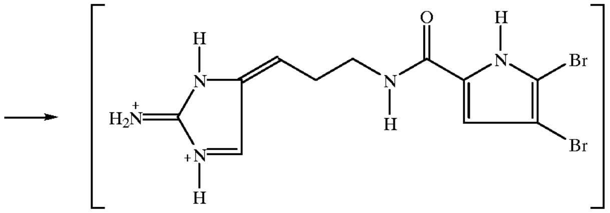

(D)

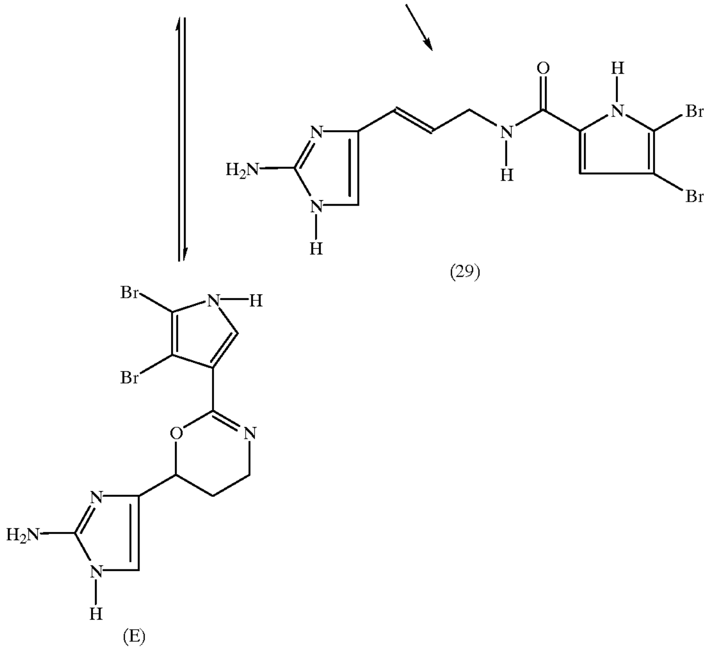

(29)

(E)

At this point, we cannot rule out the possible attack by the pyrrole nitrogen leading to the lactam (26), Scheme (4), but the N-regioselection or the C-regioselection might be controlled by altering reaction conditions. Moreover, in the absence of strong acids, species (D) could tautomerize to species (D'), Scheme (4), from which the tetracyclic alkaloids (±)-dibromophakellin (27), Scheme (4), (ref. 37, 60, 61) and (±)-dibromocantheralline (28), Scheme (4), (ref. 37) (also known as dibromoisophakellin (ref. 62)) can be derived. The relative stereochemistry of ring closures should afford the more stable cis-fused A-B ring system of the natural product. In addition, preparation of oroidine (29), Scheme (4), (ref. 37, 63, 64) could proceed by elimination of alcohol (25), Scheme (4), under basic, non-nucleophilic conditions. The generality of this strategy would be further demonstrated by synthesis of the related hymenin lactam natural products hymenialdisine (4) (R═Br), Scheme (5); debromohymenialdisine (R═H), Scheme (5); debromostevensine or monobromostevensine (30), Scheme (5), (ref. 37, 65) (also known as odiline); and axinohydantoin (31), Scheme (5), (R═Br), (ref. 8), Scheme (5). Scheme (5) shows the synthesis of hymenialdisines. The oxidation chemistry developed in Section C would be entirely applicable for transforming the forerunner hymenins (3) to its oxidative homologues (4), (30), and (31), Scheme (5).

SCHEME (5)

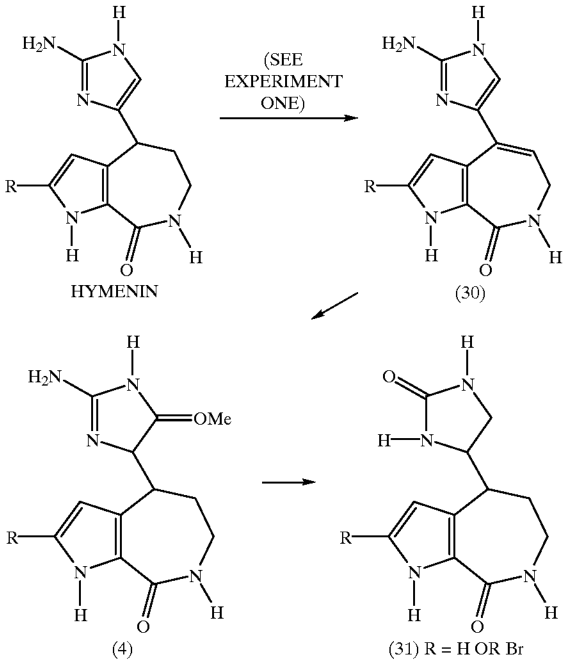

HYMENIN
(30)
(4)
(31) R = H OR Br

Sceptrin (5), oxysceptrin (6), and ageliferins (7) could result from either a [2+2] or [2+4] head to head dimerization of hymenidin (32). The only previously reported attempt to initiate [2+2] photodimerizations of (29) was unsuccessful (ref. 38). Very few experimental details were given although the investigators concluded that the biosynthesis of sceptrin (5) is unlikely to involve such photodimerizations. Based on the chemistry described in the Preliminary Results Section (Section C), as well as in this section, one possible explanation for the hymenidin photocyclization failure is the intramolecular participation of the pyrrole moiety with the photoactivated alkene. Based on this rationale, aminoimidazole (36) which lacks the pyrrole unit, would be an excellent candidate for both thermal and photodimerizations to the 6-membered and 4-membered ring systems of ageliferins and sceptrins, respectively. The preparation of the intermediate (36) should be straightforward and follows completely analogous chemistry for hydroxyalkylation of 2-aminoimidazoles. An alternative route to aminoimidazole (36) begins with the methylester of ornithine. The patented procedure [ref. 55; see also ref. 54 (preparation for 2-amino-4-ethylimidazole)] for the synthesis of 4-substituted 2-aminoimidzoles from α-aminoesters should work well for the preparation of (34). By analogy with the radical bromination chemistry of 4-substituted 2-thioimidazoles (ref. 66), aminoimidazole (34) would undergo facile bromination at the α-carbon when exposed to N-bromosuccinimide (1-bromo-2,5-pyrrolidinedione; NBS) and benzoyl peroxide. Dehydrohalogenation of the resulting α-bromo derivative (35) under basic conditions would produce the desired E-olefin (36), Scheme (6). Scheme (6) shows the synthesis of sceptrin (5), oxysceptrin (6) and ageliferins (7).

Imidazole (36) represents a versatile intermediate applicable to the synthesis of oroidin (29), hymenin (3), phakellins (27) and (28), sceptrin (5), and ageliferins (7). The recently isolated antitumor agent girolline (8) also appears to be progeny of (36). Treatment of (36) with hypochlorite would give both the syn and anti chlorohydrins of girolline (8), Scheme (7). Scheme (7) shows the synthesis of girolline (8). An alternative route to (8) would involve hydroxyalkylation of chloroaldehyde (39) derived from alkylamine. Neither of these synthetic approaches appear to be diastereoselective For the construction of (±)-saxitoxin (9), a completely analogous sequence of hydroxyalkylations is envisaged and is outlined in Scheme 8. Starting from 2-aminoimidazoles, condensation of aldehyde (40) followed by oxidation of the resulting alcohol would give ketone (42), Scheme (9). Scheme (9) shows the synthesis of saxitoxin (9). At this point, we cannot predict with certainty whether formation of this ketone will deactivate the imidazole ring toward a second, necessary hydroxyalkylation. Results from our studies (see Section C) with acetaldehyde and 2-aminoimidazole indicate that introduction of two alkyl appendages to the 4-position and 5-position of the imidazole ring can proceed by bis-hydroxyalkylation of a non-deactivated aminoimidazole. Masking the ketone as its corresponding ketal should overcome any problems associated with diminished reactivity of the imidazole moiety in (42). The addition of glycoaldehyde (or equivalent) would give intermediate (43). Activated of this intermediate to species (F), Scheme (8), followed by a double intramolecular cyclization, as in the proposed synthesis of phakellins, would afford the more stable, cis-fused (tetrahydropurine) tricyclic ring system of (±)-saxitoxin. Scheme (8) shows the retrosynthetic strategy for the construction of saxitoxin (9). Final incorporation of the carbamate moiety has previously been described (ref. 47, 48).

SCHEME (6)

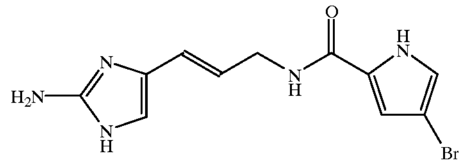

(32)

-continued
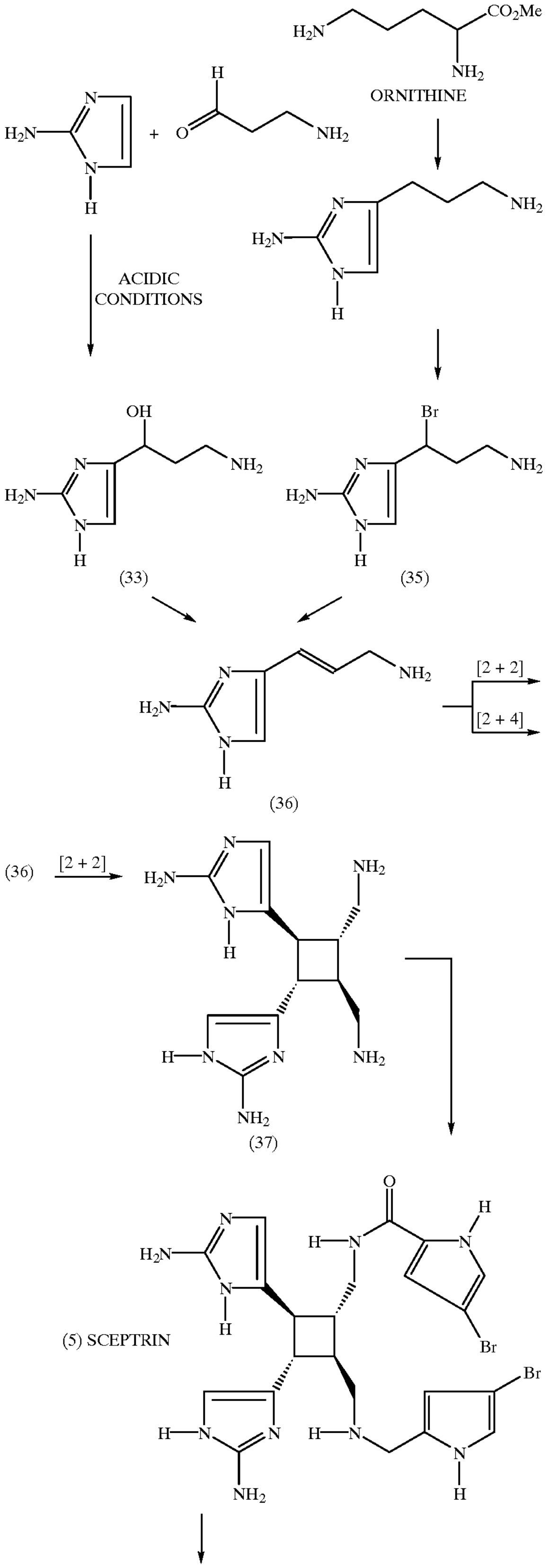
ORNITHINE
(33)
(35)
(36)
(37)
(5) SCEPTRIN
-continued
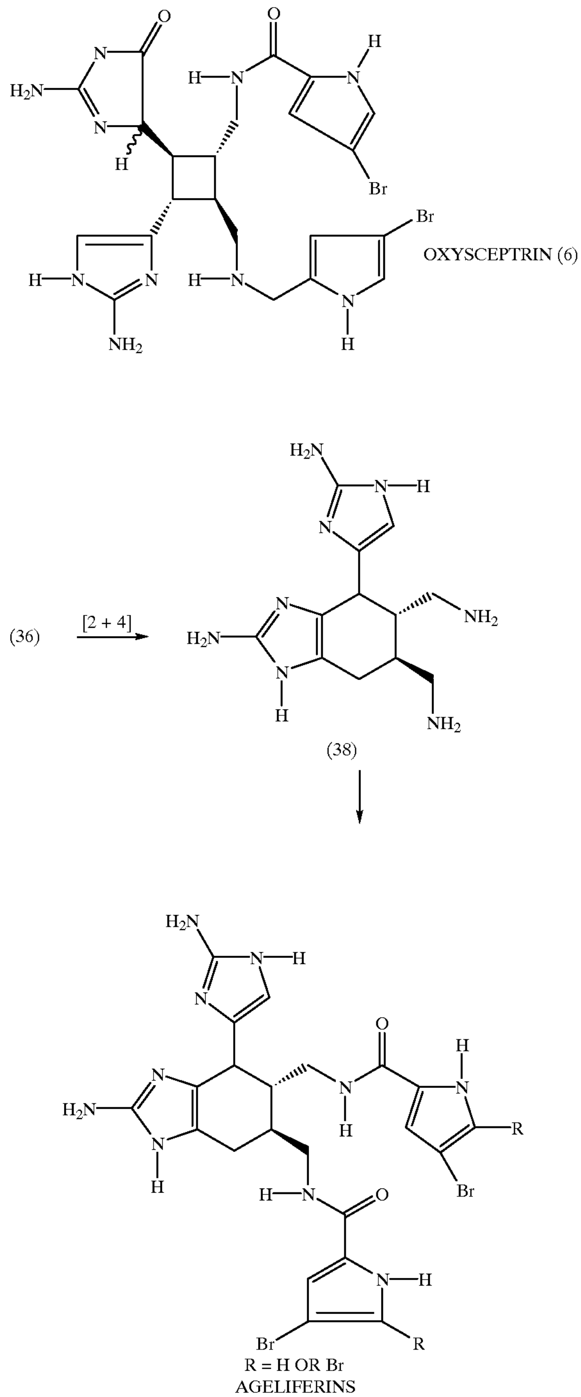
OXYSCEPTRIN (6)
(36)
(38)
R = H OR Br
AGELIFERINS SCHEME (7)
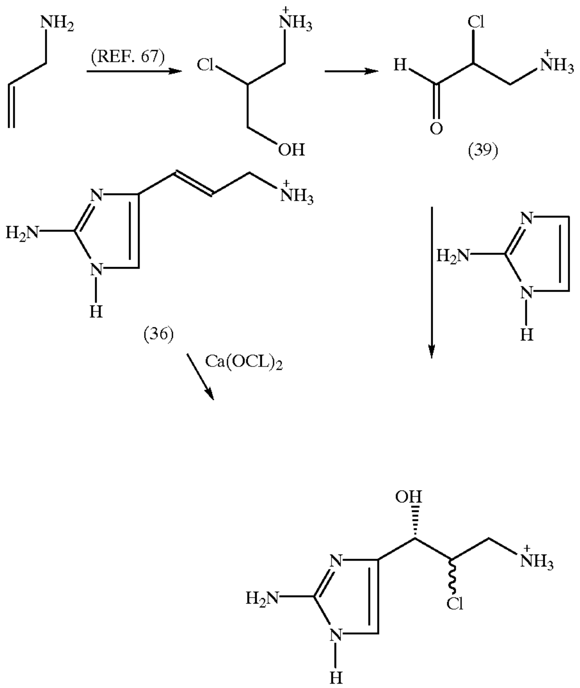
(39)
(36)
(SYN)
(8) GIROLLINE
SCHEME (8)
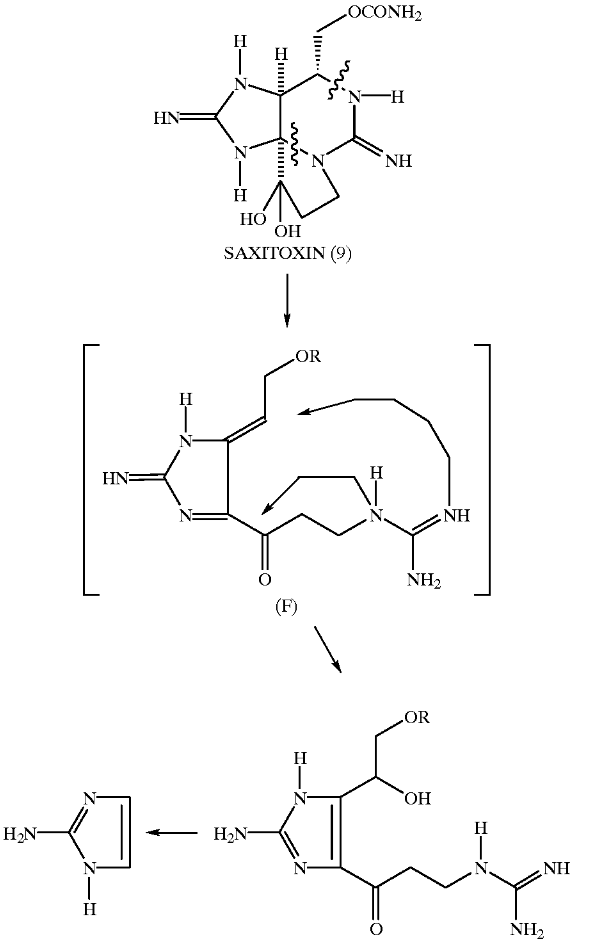
SAXITOXIN (9)
(F)
SCHEME (9)
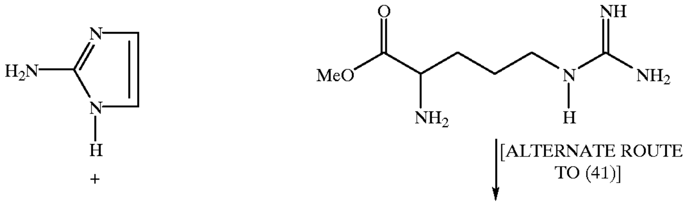

-continued

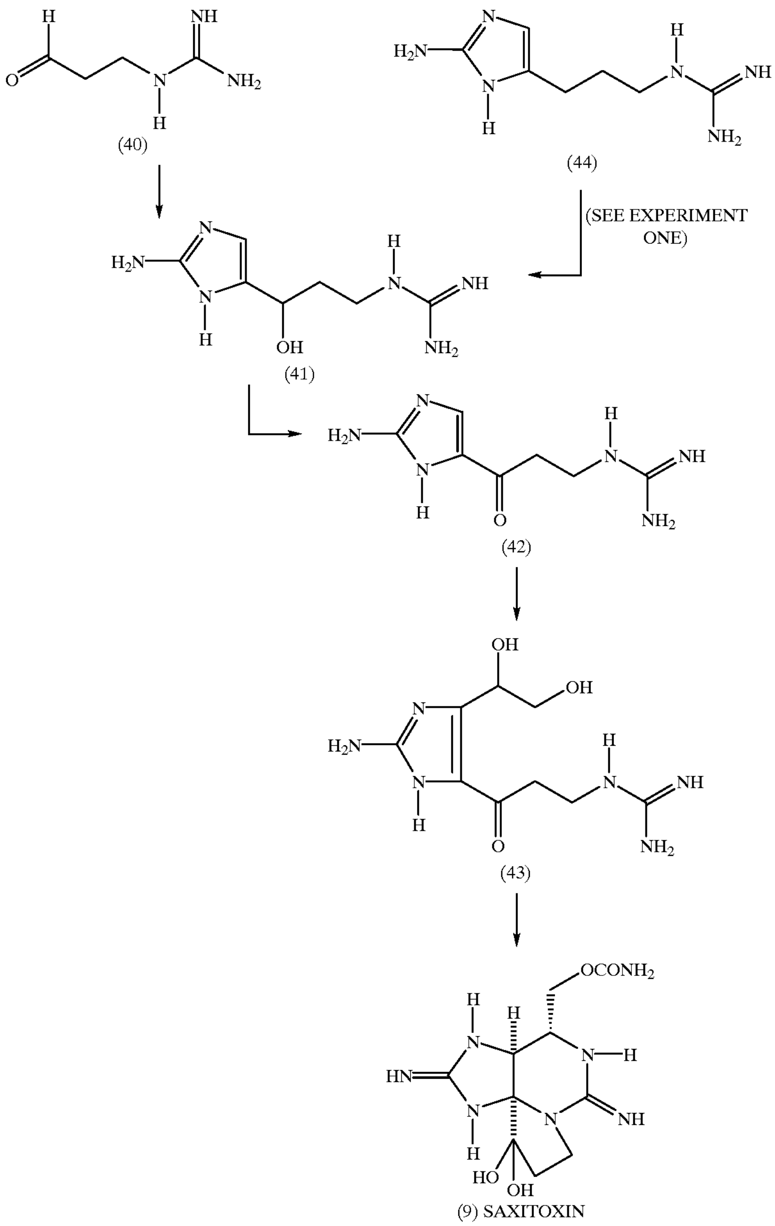

(40)

(44)

(41)

(42)

(43)

(9) SAXITOXIN

Experiment Three

FIG. 1 outlines the reaction between 2-aminoimidazoles and aldehydes. The generality of these reactions has been demonstrated with the aldehydes and aminoimidazoles shown, but by no means is the reaction limited to only these aldehydes and aminoimidazoles. The hydroxyalkylaminoimidazoles (5), (7), and (8) are valuable synthetic intermediates, or substrates, in which they can be further elaborated into structurally diverse derivatives. For the synthesis of imidazoazepines (9) (eq. IV), this reaction type can be extended to afford a number of fused bicyclic 2-aminoimidazoles of different ring sizes. In the present case, a 3-carbon amino appendage affords the 7-membered ring imidazoazepines (9) and (10). In principle, a 2-carbon or 4-carbon amino appendage (etc . . . ) would give 6- and 8- membered ring aminoimidazoles, respectively. These reactions are simple to perform and provide easy access to a large number of structurally unique 2-aminoimidazoles.

FIG. 1 depicts R groups for the compounds made and described. In particular, the compounds made and described include, referring to FIG. 1, the following: (6a), (5b), (6b (α-methyl)), (6b (β-methyl)), (5c), (6c (mixture of diastereomers)), (5d), (6d (α-isopropyl)), (6d (β-isopropyl)), (5e), (6e), (6f (mixture of diastereomers)), (7a), (7b), (7c), (7d), (7e), (7f), (8a), (8g), (9b), (9c), (9d), (9e), (9f), (9g), (9h), and (10h), wherein the letters following the compound number indicates the designation of the R substituted group. R in FIG. 1 include the following designations: H (a); $CH_3$ (b); $CH_2CH_3$ (c); $CCH(CH_3)_2$ (d); $CH_2Ph$ (e); $CH_2CH(CH_3)_2$ (f); $CH_2OCH_2Ph$ (g); $CH_2Cl$ (h).

Figure 2:
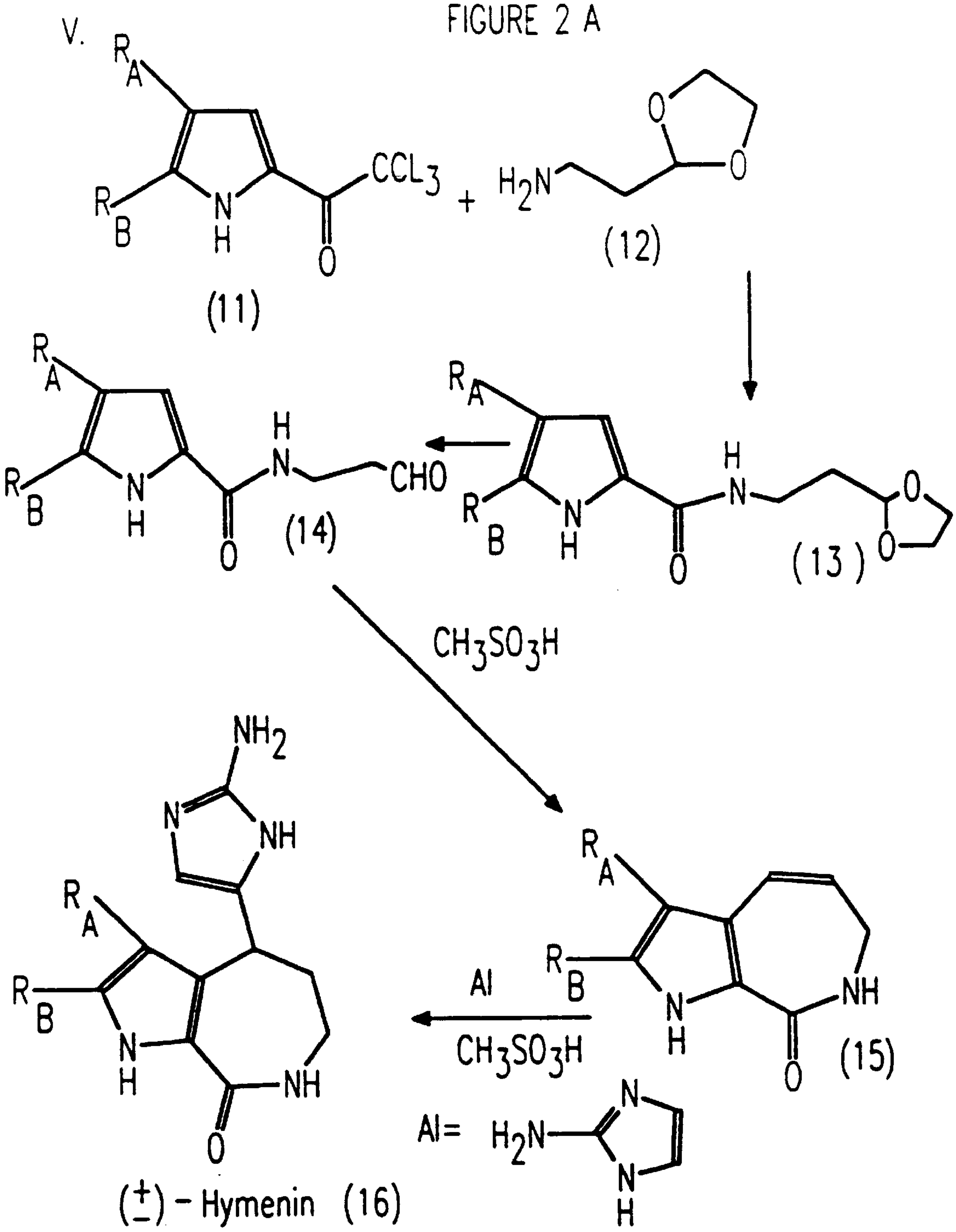
FIG. 2A depicts the synthesis of the α-adrenoceptor antagonist (±)-hymenin (16), involving an acid-promoted intramolecular cyclization and dehydration of pyrrole aldehyde (14) to give the cyclic olefin (15), and the coupling of olefin (15) with 2-aminoimidazole (AI) under acidic conditions to give (±)-hymenin.
FIG. 2B depicts the the synthesis of the α-adrenoceptor antagonist (±)-hymenin (16), showing that the two steps in FIG. 2A can be combined into one operation in which the combination of aldehyde (14) and AI produces (±)-hymenin (16) in a 'single pot'.
Figure 2:
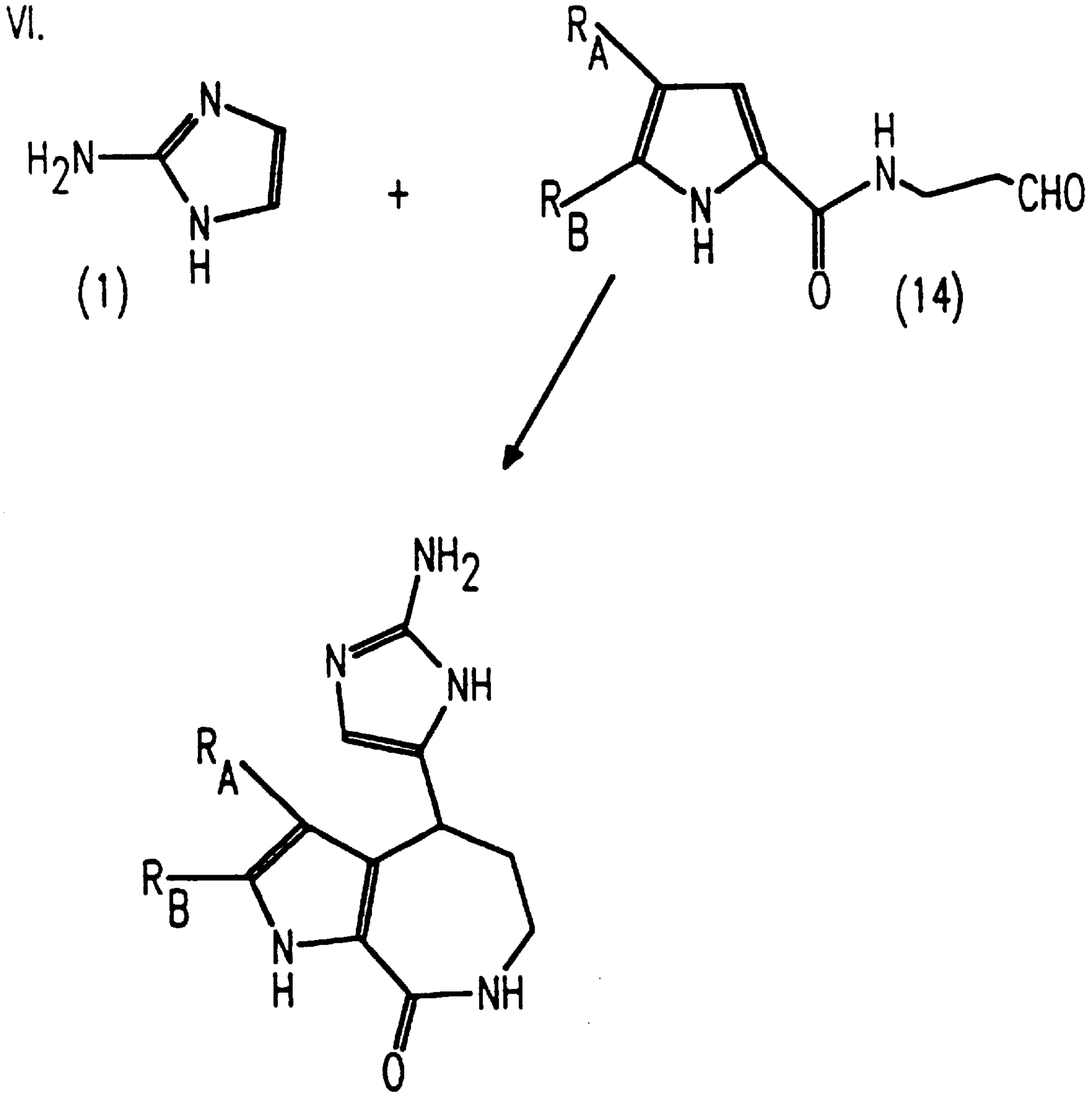
Figure 3:
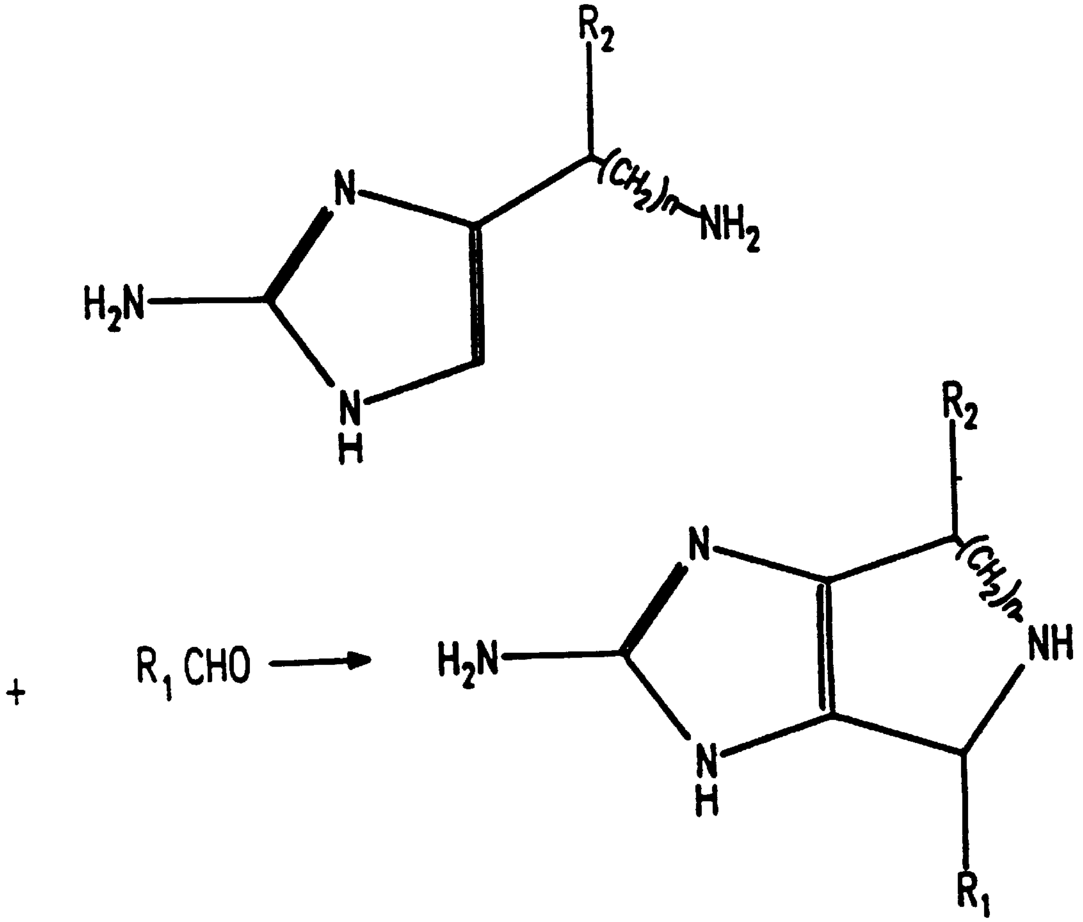
FIG. 3A depicts the process for preparing the bicyclic aminoimidazole compound of the subject invention.
FIG. 3B depicts the process for preparing the hydroxyalkyl aminoimidazole compound of the subject invention.
FIG. 3C depicts the process for preparing the bicyclic pyrrole compound of the subject invention.
Figure 3:
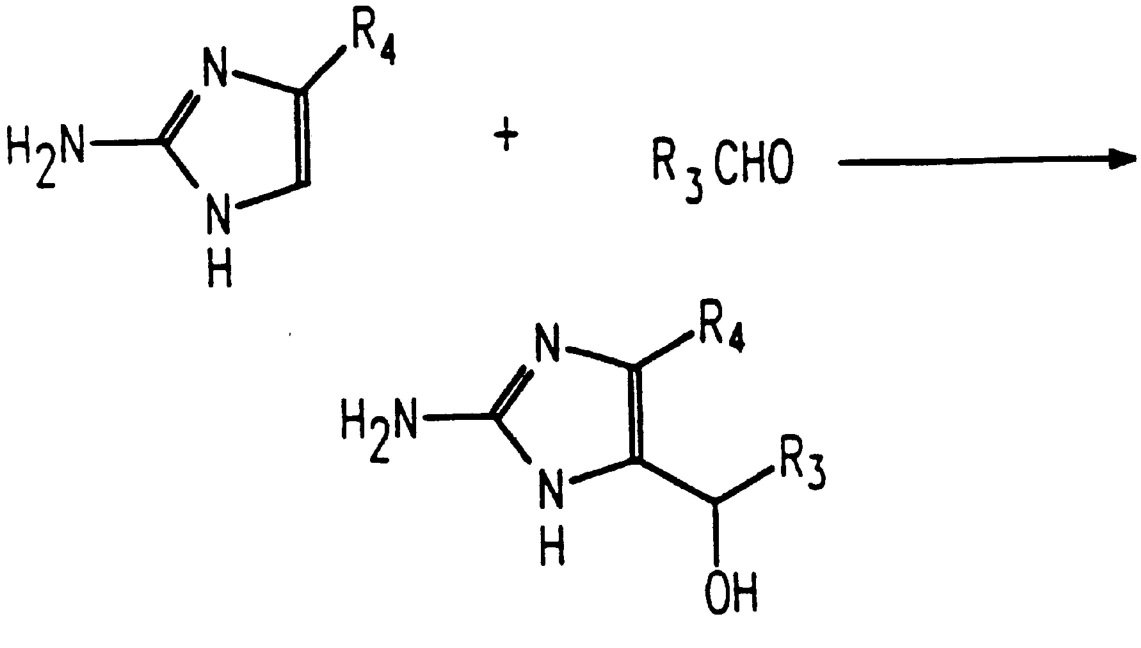

FIG. 2 depicts the synthesis of the α-adrenoceptor antagonist (±)-hymenin (16), a 2-aminoimidazole marine natural product with antihypertension activity. There are two important reactions in this synthetic scheme, neither of which has been previously described. The first is an acid-promoted intramolecular cyclization and dehydration of pyrrole-aldehyde (14) to give the cyclic olefin (15). As in the imidazoazepine series, this reaction can also be generalized to include a wide variety of substituted pyrroles differing in $R_A$ and $R_B$ as well as in the size of the newly formed ring (FIG. 3). The second equally important step in this synthesis involves the coupling of olefin (15) with 2-aminoimidazole (AI) under acidic conditions to give (±)-hymenin (16). This reaction is yet another example that illustrates the utility of using 2-aminoimidazole (AI) in combination with active electophiles as starting materials for the synthesis of 2-aminoimidazole derived natural products. Moreover, these two steps can be combined into one operation in which the combination of aldehyde (14) and AI produces (±)-hymenin (16) in a 'single pot' (eq. VI). This eliminates the need for isolation of potential intermediate (15). As for FIG. 1, FIG. 2 depicts the synthesis of compounds made and described below.

As discussed earlier, a large number of 2-aminoimidazole alkaloids have been isolated from marine sources. Most importantly, these metabolites have been shown to possess a myriad of biological activities.

FIG. 3 depicts generalized schemes for the reaction between 2-aminoimidazoles and aldehydes.

FIG. 3A depicts the process for preparing the bicyclic aminoimidazole compound of the subject invention, wherein n is an integer from 0 to about 5;

wherein $R_1$ is H; a $C_1$ to about $C_{10}$ alkyl group, which is a primary alkyl group, or a secondary branched alkyl group, or a tertiary branched alkyl group wherein the tertiary carbon of the tertiary branched alkyl group is separated from the ring structure of the bicyclic aminoimidazole compound by at least one carbon atom; a phenyl group; a thiophenyl group; a pyrrolyl group; a furanyl group; a benzyl group; or a pyridyl group;

which alkyl, phenyl, thiophenyl, pyrrolyl, furanyl, benzyl, or pyridyl groups are substituted or unsubstituted; and wherein $R_2$ is H; a $C_1$ to about $C_{10}$ alkyl group, which is a straight chain alkyl group, or a branched alkyl group; or a phenyl group; which alkyl or phenyl groups are substituted or unsubstituted.

The alkyl, phenyl, thiophenyl, pyrrolyl, furanyl, benzyl, or pyridyl groups of FIG. 3A may be substituted with halogen, alcohol, alkoxy, dialkyl amine, alkyl aryl amine, diaryl amine, thiol, sulfide, or nitro groups.

FIG. 3B depicts the process for preparing the hydroxyalkyl aminoimidazole compound of the subject invention, wherein;

when $R_3$ is a $C_1$ to about $C_{10}$ alkyl group, which is a primary alkyl group, a secondary branched alkyl group, or a tertiary branched alkyl group wherein the tertiary carbon of the tertiary branched alkyl group is separated from the ring structure of the hydroxyalkyl aminoimidazole compound by at least one carbon atom; which alkyl groups are substituted or unsubstituted;

then $R_4$ is H, a $C_1$ to about $C_{10}$ straight chain alkyl group or branched alkyl group to which guanidine is attached wherein the guanidine is separated from the ring structure of the hydroxyalkyl aminoimidazole compound by at least one carbon atom, a $C_1$ to about $C_{10}$ straight chain alkyl group or branched alkyl group, a phenyl group, a thiophenyl group, a pyrrolyl group, a furanyl group, a benzyl group, or a pyridyl group; which alkyl to which guanidine is attached, alkyl, phenyl, thiophenyl, pyrrolyl, furanyl, benzyl, or pyridyl groups are substituted or unsubstituted; or;

when $R_3$ is H;

then $R_4$ is a $C_1$ to about $C_{10}$straight chain alkyl group or branched alkyl group to which guanidine is attached wherein the guanidine is separated from the ring structure of the hydroxyalkyl aminoimidazole compound by at least one carbon atom, a $C_1$ to about $C_{10}$ straight chain alkyl group or branched alkyl group, a phenyl group, a thiophenyl group, a pyrrolyl group, a furanyl group, a benzyl group, or a pyridyl group; which alkyl to which guanidine is attached, alkyl, phenyl, thiophenyl, pyrrolyl, furanyl, benzyl, or pyridyl groups are substituted or unsubstituted.

Regarding the hydroxyalkyl aminoimidazole compound of the subject invention, the subject invention provides that the alkyl to which guanidine is attached, alkyl, phenyl, thiophenyl, pyrrolyl, furanyl, benzyl, or pyridyl groups may be substituted with halogen, alcohol, alkoxy, dialkyl amine, alkyl aryl amine, diaryl amine, thiol, or sulfide groups.

Figure 3C:
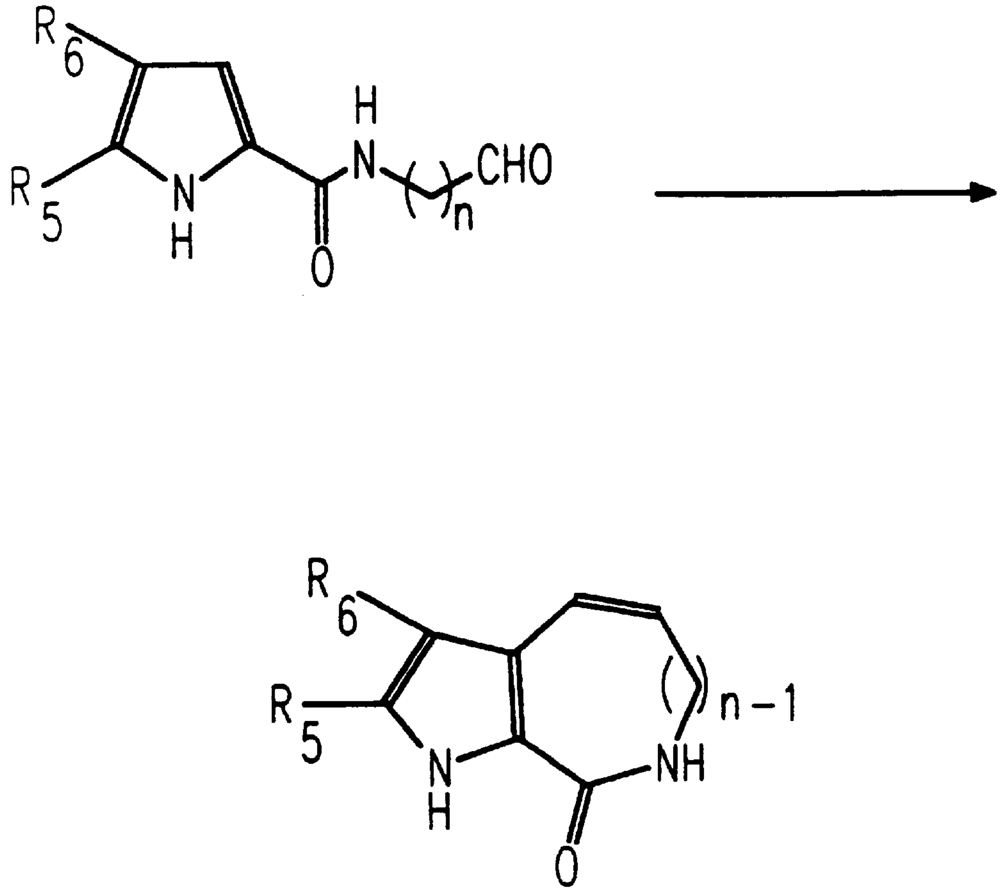

FIG. 3C depicts the process for preparing the bicyclic pyrrole compound of the subject invention, wherein, n is an integer from 1 to about 6;

wherein $R_5$ and $R_6$ are the same or different, and are H; a $C_1$ to about $C_{10}$ straight chain alkyl group or branched alkyl groups, which alkyl groups are substituted or unsubstituted; or halogen.

Regarding bicyclic pyrrole compound, the subject invention provides that the alkyl groups may be substituted with halogen, alcohol, alkoxy, dialkyl amine, alkyl aryl amine, diaryl amine, thiol, or sulfide groups.

General Procedure for the Preparation of Hydroxyalkylaminoimidazoles (5, 7, 8) and Tetrahydropurines (6)

To a stirred solution of 2-aminoimidazole sulfate (1), (1 mmol), in 5 ml of water was added sodium carbonate (0.6 mmol) or sodium bicarbonate at 25° C. After 10 min., the requisite aldehyde (a-h) (1.2 mmol) was added. In cases where the aldehyde was not soluble in water, 5 ml of methanol or ethanol was added to solubilize the mixture. After stirring for 2 to 72 hours at 25° C. the reaction mixture was concentrated under reduced pressure and the resulting residue purified by silica gel chromatography using methylene chloride:methanol (sat. ammonia) 8:2 or 9:1 as the eluent. Yields of 30–40% were obtained for hydroxyalkylaminoimidazoles (5). Continued elution with 2:8 methylene chloride:methanol (sat. ammonia) or with methanol (sat. ammonia) afforded the tetrahydropurine adducts (6) in 25–40% yields. Hydroxyalkylaminoimidazoles (7) and (8) were prepared in 75–80% yields from 4-ethyl-2-aminoimidazole hydrochloride (2) and 4-guanidinopropyl-2-aminoimidazole hydrochloride (3) (ref. 54), respectively, by the method described above. Purification by silica gel chromatography of hydroxyalkylaminoimidazoles (8) was accomplished using a mixture of ethanol:formic acid:water (9:0.5:0.5) as the eluent.

Tetrahydropurine (6a of FIG. 1)

mp 95° C. (dec)

$^1$H NMR (300 MHz, $CD_3OD$) δ3.36 (dd, J=12.0 Hz, 3.3 Hz, 1H), 3.44 (dd, J=12.0 Hz, 3.3 Hz, 1H), 4.44 (dt, J=8.0 Hz, 3.3 Hz, 1H), 5.79 (d, J=8.0 Hz, 1H), 6.55 (d, J=1.7 Hz, 1H), 6.74 (d, J=1.7 Hz, 1H).

$^{13}$C NMR (75 MHz, $CD_3OD$) δ43.1, 57.3, 69.2, 113.7, 125.6, 150.0, 166.1.

IR (Nujol) $cm^{-1}$ 3295, 2494, 1588, 1403, 1112, 806, 692.

MS (DCI, $CH_4$) m/z 179 ($MH^+$, 100), 105 (24), 96 (50), 77 (12).

4-(1-Hydroxyethyl)-2-Aminoimidazole (5b of FIG. 1) (Known Compound)

colorless solid, $^1$H NMR (300 MHz, $CD_3OD$) δ1.42 (d, J=6.4 Hz, 3H), 4.66 (q, J=6.4 Hz, 1H), 6.40 (s, 1H).

$^{13}$C NMR (75 MHz, DMSO-d6) δ23.0, 62.0, 110.5, 136.6, 148.8.

Tetrahydropurine (6b of FIG. 1) (α-methyl)

$^1$H NMR (300 MHz, $CD_3OD$) δ1.25 (d, J=5.3 Hz, 3H), 3.46 (p, J=5.3 Hz, 1H), 3.98 (dd, J=5.3 and 7.8 Hz, 1H), 5.71 (d, J=7.8 Hz, 1H), 6.55 (d, J=1.7 Hz, 1H), 6.76 (d, J=1.7 Hz, 1H).

IR (Nujol) $cm^{-1}$ 3183, 1574, 1428, 1070.

MS (DCI, $CH_4$) m/z 193 ($MH^+$, 30), 140 (12), 124 (20), 112 (60), 84 (100).

Tetrahydropurine (6b of FIG. 1) (β-methyl)

$^1$H NMR (300 MHz, $CD_3OD$) δ1.35 (d, J=6.7 Hz, 3H), 3.54 (m, 1H), 4.24 (qd, J=2.3 and 7.9 Hz, 1H), 5.75 (d, J=7.9 Hz, 1H), 6.53 (d, J=1.7 Hz, 1H), 6.71 (d, J=1.7 Hz, 1H).

IR (Nujol) $cm^{-1}$ 3236, 1574, 1416, 1088.

MS (DCI, $CH_4$) m/z 193 ($MH^+$, 20), 167 (25), 124 (30), 112 (45), 84 (100).

4-(1-Hydroxypropyl)-2-Aminoimidazole (5c of FIG. 1)

mp 93–96° C. (dec).

$^1$H NMR (300 MHz, $CD_3OD$) δ0.90 (t, J=7.4 Hz, 3H), 1.76 (m, 2H), 4.37 (t, J=6.7 Hz, 1H), 6.40 (s, 1H).

$^{13}$C NMR (75 MHz, $CD_3OD$) δ10.5, 30.4, 70.0, 113.2, 136.6, 150.9.

IR (Nujol) $cm^{-1}$ 3186, 1629, 1574,1402, 1242, 1095, 1044, 958, 810, 694, 664.

MS (DCI, $CH_4$) m/z 142 ($MH^+$, 75), 124 (100), 112 (48), 84 (92).

Tetrahydropurine (6c of FIG. 1 ) (Mixture of Diastereomers)

mp 86° C. (dec)

$^1$H NMR (400 MHz, $CD_3OD$) δ0.99 (d, J=7.4 Hz, 3H), 1.07 (t, J=7.4 Hz, 3H), 1.40–1.50 (m, 1H), 1.50–1.55 (m, 1H), 1.73 (m, 2H), 3.31 (m, 2H), 4.17 (dd, J=4.0 and 7.9 Hz, 1H), 4.33 (dd, J=2.2 and 7.9 Hz, 1H), 5.64 (d, J=7.9 Hz, 1H), 5.72 (d, J=7.9 Hz, 1H), 6.53 (d, J=1.7 Hz, 1H), 6.71 (d, J=1.7 Hz, 1H).

$^{13}$C NMR (400 MHz, $CD_3OD$) δ10.5, 10.6, 26.1, 26.8, 55.0, 55.7, 60.5, 61.0, 69.7, 71.3, 119.5, 125.3, 148.5, 149.9, 163.3, 164.4

IR (Nujol) $cm^{-1}$ 3220, 2486, 2236, 1651, 1586, 1409, 1238, 1105, 802, 694.

MS (DCI,$CH_4$) m/z 207 ($MH^+$, 25), 167 (12), 152 (18), 124 (100), 112 (20).

4-(1-Hydroxyisobutyl)-2-Aminoimidazole (5d of FIG. 1)

mp 95° C. (dec).

$^1$H NMR (300 MHz, $D_2O$) δ0.80 (d, J=6.8 Hz, 3H), 0.95 (d, J=6.7 Hz, 3H), 1.97 (m, 1H), 4.21 (d, J=7.8 Hz, 1H), 6.56 (s, 1H).

IR (Nujol) $cm^{-1}$ 3199, 1563, 1408, 1279, 1090, 1003, 745, 664.

MS (DCI, $CH_4$) m/z 156 ($MH^+$, 25), 138 (100), 112 (20).

Tetrahydropurine (6d of FIG. 1) (α-isopropyl)

mp 65° C. (dec).

$^1$H NMR (300 MHz, $D_2O$) δ1.05 (d, J=6.75 Hz, 3H), 1.11 (d, J=6.65 Hz, 3H), 1.85 (m, 1H), 3.12 (dd, J=9.6 Hz, 1.9 Hz, 1H), 4.64 (dd, J=8.1 Hz, 1.9 Hz, 1H), 5.86 (d, J=8.1 Hz, 1H), 6.66 (d, J=1.8 Hz, 1H), 6.81(d, J=1.8 Hz, 1H).

IR (Nujol) $cm^{-1}$ 3198, 1731, 1694, 1583, 1392, 1271, 1119, 1072, 740, 694.

MS (DCI, $CH_4$) m/z 221 ($MH^+$, 25), 138 (25), 84 (100).

Tetrahydropurine (6d of FIG. 1) (β-isopropyl)

mp 65° C. (dec).

$^1$H NMR (300 MHz, $D_2O$) δ0.87 (d, J=6.7 Hz, 3H), 0.97 (d, J=6.7 Hz, 3H), 1.75 (m, 1H), 3.27 (dd, J=7.7 Hz, 2.3 Hz, 1H), 4.55 (dd, J=7.9 Hz, 2.3 Hz, 1H), 5.79 (d, J=7.9 Hz, 1H), 6.62 (d, J=1.7 Hz, 1H), 6.77 (d, J=1.7 Hz, 1H).

IR (Nujol) $cm^{-1}$ 3176, 1732, 1694, 1592, 1556, 1504, 1416, 1271, 1121, 1072, 691, 656.

MS (DCI, $CH_4$) m/z 221 ($MH^+$, 62), 177 (25), 166 (62), 149 (45), 84 (100).

4-(1-Hydroxyphenylethyl)-2-Aminoimidazole (5e of FIG. 1)

mp 90° C. (dec).

$^1$H NMR (300 MHz, $CD_3OD$) δ2.96 (dd, J=7.6 Hz, 13.5 Hz, 1H), 3.10(dd, J=6.1 Hz, 13.5 Hz, 1H), 4.66 (dd, J=6.1 Hz, 7.6 Hz, 1H), 6.33 (s, 1H), 7.19 (m, 5H).

$^{13}$C NMR (75 MHz, $CD_3OD$) δ45.8, 71.7, 114.5, 128.6, 130.6, 132.1, 138.5, 141.7, 152.6.

IR (Nujol) $cm^{-1}$ 3131, 1732, 1614, 1568, 1493, 1417, 1316, 1120, 1054, 1031, 986, 863, 743, 697.

MS (DCI, $CH_4$) m/z 204 ($MH^+$, 100).

Tetrahydropurine (6e of FIG. 1)

colorless solid, mp 60° C. (dec).

$^1$H NMR (300 MHz, $CD_3OD$) δ3.00 (d, J=7.5, 2H), 3.66 (m, 1H), 4.18 (dd, J=7.8 Hz, 2.0 Hz, 1H), 5.65 (d, J=7.8 Hz, 1H), 6.52 (d, J=1.6 Hz, 1H), 6.69 (d, J=1.6 Hz, 1H), 7.35 (m, 5H).

IR (Nujol) $cm^{-1}$ 3308, 1644, 1574, 1428, 1360, 1088, 699.

MS (DCI, $CH_4$) m/z 269 ($MH^+$, 12), 180 (25), 101 (30), 84 (100).

Tetrahydropurine (6f of FIG. 1) (Mixture of Diastereomers)

$^1$H NMR (300 MHz, $CD_3OD$) δ0.93 (d, J=4.3 Hz, 3H), 0.95 (d, J=4.3 Hz, 3H), 0.99 (d, J=4.7 Hz, 3H), 1.01 (d, J=4.7 Hz, 3H), 1.25–1.50 (m, 2H), 1.50–1.70 (m, 2H), 1.70–1.90 (m, 2H), 3.31 (m, 1H), 3.50 (m, 1H), 4.06 (dd, J=7.8 and 4.0 Hz, 1H), 4.26 (dd, J=7.8 Hz, 2.2 Hz, 1H), 5.63(d, J=7.8 Hz, 1H), 5.72 (d, J=7.8 Hz, 1H), 6.53 (d, J=1.7 Hz, 1H), 6.70 (d, J=1.7 Hz, 1H).

IR (Nujol) $cm^{-1}$ 3204, 1692, 1590, 1288, 1102, 634.

MS (DCI,CH4) m/z 235 ($MH^+$,36), 152 (18), 101 (13), 84 (100).

4-Ethyl-5-(1-Hydroxymethyl)-2-Aminoimidazole (7a of FIG. 1)

$^1$H NMR (300 MHz, $CD_3OD$) δ1.20 (t, J=7.6 Hz, 3H), 2.54 (q, J=7.6 Hz, 2H), 4.41 (s, 2H).

$^{13}C$ NMR (75M Hz, $CD_3OD$) δ14.2, 17.7, 53.5, 122.2, 126.9, 148.1.

IR (Nujol) $cm^{-1}$ 3171, 1732, 1682, 1590, 1538, 1408, 1336, 1130, 1071, 1006, 608.

MS (DCI, $CH_4$) m/z 142 ($MH^+$, 65), 124 (90), 120 (50), 103 (100).

4-Ethyl-5-(1-Hydroxyethyl)-2-Aminoimidazole (7b of FIG. 1)

mp 80° C. (dec).

$^1H$ NMR (300 MHz, $D_2O$) δ1.11(t, J=7.6 Hz, 3H), 1.44 (d, J=6.7 Hz, 3H), 2.48 (q, J=7.6 Hz, 2H), 4.89 (q, J=6.7 Hz, 1H).

$^{13}C$ NMR (75 MHz, $D_2O$) δ16.6, 20.1, 24.0, 63.7, 129.9, 131.9, 150.6).

IR (Nujol) $cm^{-1}$ 3091, 1682, 1643, 1574, 1496, 1455, 1368, 1304, 1130, 1074, 1015, 895, 737, 647.

MS (DCI, $CH_4$) m/z 166 ($MH^+$, 12), 138 (100).

4-Ethyl-5-(1-Hydroxypropyl)-2-Aminoimidazole (7c of FIG. 1)

mp 90° C. (dec).

$^1H$ NMR (400 MHz, DMSO-$d_6$) δ0.72 (t, J=7.2 Hz, 3H), 1.02 (t, J=7.4 Hz, 3H), 1.60 (m,1H), 2.31 (q, J=7.4 Hz, 2H), 4.26 (t, J=6.9 Hz, 1H).

IR (Nujol) $cm^{-1}$ 3178, 1634, 1574, 1416, 1000, 953, 692, 550.

MS (DCI, $CH_4$) m/z 170 ($MH^+$, 100), 152 (48).

4-Ethyl-5-(1-Hydroxyisopropyl)-2-Aminoimidazole (7d of FIG. 1)

mp 110° C. (dec).

$^1H$ NMR (400 MHz, DMSO-$d_6$) δ0.83 (m,6H), 1.05 (t, J=7.5 Hz, 3H), 1.45 (m, 2H), 1.55 (m, 1H), 2.32 (q, J=7.5 Hz, 2H), 4.32 (t, J=6.9 Hz, 1H)

IR (Nujol) $cm^{-1}$ 3190, 1640, 1580, 1494, 1417, 1309, 1130, 1048, 974, 952, 846, 739, 692.

MS (DCI, $CH_4$) m/z 198 ($MH^+$, 100), 180 (80), 112 (20), 90 (42), 89 (22).

4-Ethyl-5-(1-Hydroxyphenylethyl)-2-Aminoimidazole (7e of FIG. 1)

mp 95° C. (dec).

$^1H$ NMR (400 MHz, DMSO-$d_6$) δ0.78 (t, J=7.4 Hz, 3H), 2.12 (m, 2H), 2.89 (dd, J=7.7 Hz, 13.0 Hz, 1H), 2.99 (dd, J=6.7 Hz, 13.0 Hz, 1H), 4.55 (dd, J=6.7 Hz, 7.7 Hz, 1H), 7.06–7.20 (m, 5H).

$^{13}C$ NMR (100 MHz, DMSO-$d_6$) δ14.7, 18.3, 43.5, 66.3, 125.4, 125.9, 128.8, 129.4, 139.4, 148.2.

IR (Nujol) $cm^{-1}$ 3208, 2940, 1745, 1633, 1574, 1494, 1417, 1298, 1237, 1122, 1045, 992, 856, 748, 692.

MS (DCI, $CH_4$) m/z 232 ($MH^+$, 100), 214 (55), 138 (22), 112 (72).

4-Ethyl-5-(1-Hydroxyisobutyl)-2-Aminoimidazole (7f of FIG. 1)

colorless solid, mp 98° C. (dec).

$^1H$ NMR (400 MHz, DMSO-$d_6$) δ0.66 (d, J=6.8 Hz, 3H), 0.94 (d, J=6.6 Hz, 3H), 1.06 (t, J=7.5 Hz, 3H), 1.81 (m, 1H), 2.34 (g, J=7.5 Hz, 2H), 4.01 (d, J=8.2 Hz, 1H).

$^{13}C$ NMR (100 MHz, DMSO-$d_6$) δ14.6, 17.7, 18.9, 19.3, 33.5, 69.6, 124.1, 127.0, 147.2.

IR (Nujol) $cm^{-1}$ 3184, 2947, 1682, 1633, 1574, 1495, 1403, 1328, 1016, 785.

MS (DCI, $CH_4$) m/z 183 ($MH^+$, 100), 166 (36), 112 (18).

4-(3-Guanidinopropyl)-5-(1-Hydroxymethyl)-2-Aminoimidazole (8a of FIG. 1) ($H_2SO_4$ Salt)

mp>250° C.

$^1H$ NMR (300 MHz, $D_2O$) δ1.88 (m, 2H), 2.63 (t, J=7.3 Hz, 2H), 3.19 (t, J=6.7 Hz, 2H), 4.47 (s, 2H);

$^{13}C$ NMR (in $D_2O$) δ22.57, 29.69, 42.75, 54.82, 123.6, 126.4, 149.2, 159.5.

4-(3-Guanidinopropyl-5-(1-Hydroxy-2-Benzyloxyethyl)-2-Aminoimidazole (8g of FIG. 1) ($2HCO_2H$ Salt)

Yellow oil, $^1H$ NMR (300 MHz, $D_2O$) δ1.67 (m, 2H), 2.44 (t, J=7.5 Hz, 2H), 3.00 (t, J=6.9 Hz, 2H), 3.58 (dd, J=5.8 Hz, 10.3 Hz, 1H), 3.69 (dd, J=5.8 Hz, 10.3 Hz, 2H), 4.49 (dx2, J=11.9 Hz, 2H), 4.75 (t, J=5.8 Hz, 1H), 7.25 (m, 2H), 7.31 (m, 3H), 8.40 (bs, 2H);

$^{13}C$ NMR (in $D_2O$) δ21.6, 29.2, 41.3, 64.4, 73.7, 74.3, 123.7, 124.0, 128.8, 129.0 (x2), 129.4(x2), 139.2, 148.7, 158.7, 170.7 (x2).

MS (DCI, $CH_4$) m/z 333 ($MH^+$).

Data For (8g of FIG. 1)

$^1H$ NMR (300 M Hz, $D_2O$) d 1.87–1.80 (m, 2H), 2.60 (t, J=7.5 Hz, 2H), 3.16 (t, J=6.8 Hz, 2H), 3.70 (dd, J=11.5 and 6.3 Hz, 1H), 3.75 (dd, J=11.5 and 6.2 Hz, 1H), 4.92 (t, J=6.2 Hz, 1H), 8.41 (s, 2H).

General Procedure for the Preparation of Imidazoazepines (9 and 10)

To a stirred solution of 4-(3-aminopropyl)-2-aminoimidazole dihydrochloride (4) (10.0 mmol) (ref. 54) and sodium carbonate (12.0 mmol) in 6 ml of a 1:1 water/ethanol mixture was added the requisite aldehyde (b-h) (12 mmol). Stirring continued until TLC [$CH_2Cl_2$/MeOH (sat. $NH_3$), 8/2] indicated the disappearance of 4-(3-aminopropyl)-2-aminoimidazole (4) (about 30 min.). The mixture was then filtered to remove any precipitates that formed and the solvent/filtrate was evaporated under reduced pressure. The reaction mixture was purified by silica gel chromatography with $CH_2Cl_2$/MeOH($NH_3$), 8/2, as the eluent to afford a light-yellow oil. The product was dissolved in MeOH saturated with HCl and evaporated under reduced pressure yielding the dihydrochloride salt as a colorless, hygroscopic solid. Yields ranged from 80–90%.

Imidazoazepine (9b of FIG. 1)

(2HCl salt) mp 237–238° C., 85% yield;

$^1H$ NMR (freebase) δ1.49 (d, 3H, J=7.0 Hz), 1.92 (m, 2H), 2.69 (t, 2H, J=5.84 Hz), 3.16 (ddd, 1H, J=14.0, 7.7, 3.7 Hz), 3.45 (ddd, 1H, J=14.0, 7.1, 3.5 Hz), 4.23 (q, 1H, J=7.0 Hz);

(2HCl salt) $^1H$ NMR δ1.43 (d, 3H, J=7.0 Hz), 2.1 (m, 2H), 2.81 (t, 2H, J=6.0 Hz), 3.45 (ddd, 1H, J=14.2, 8.25, 3.3 Hz), 3.67 (ddd, 1H, J=14.2, 7.5, 3.5), 4.67 (q, 1H, J=7.0 Hz);

$^{13}C$ NMR (freebase) δ20.4, 26.8, 28.3, 49.7, 54.3, 129.3, 131.3, 150.0;

IR (freebase) 3320, 2764, 1574, 1494, 1415, 1315, 1021, 666;

MS (m/z, rel. intensity) 195 ($MH^+$, 100), 167 (10), 151 (30), 138 (40), 124 (20), 115 (8), 85 (12), 70 (15).

Imidazoazepine (9c of FIG. 1)

(2HCl salt) mp 72–75° C., 85% yield;

$^1$H NMR (freebase) δ1.27 (t, 3H, J=7.0 Hz), 2.10 (m, 4H), 2.45 (m, 2H), 3.24 (m, 1H), 3.47 (m, 1H), 4.00 (t, 1H, J=6.3 Hz);

(2HCl salt) $^1$H NMR δ1.00 (t, 3H, J=7.4 Hz), 2.03 (m, 2H), 2.77 (m, 2H), 3.55 (m, 2H), 4.42 (t, 1H, J=7.4 Hz);

$^{13}$C NMR (freebase) δ13.36, 28.29, 29.20, 31.41, 49.13, 59.54, 130.98, 133.75, 150.00;

IR (2HCl salt) 3000, 1720, 1625, 1480, 1200, 800, 700; MS (m/z, rel. intensity) 181 ($MH^+$, 100), 151 (7), 78 (5).

Imidazoazepine (9d of FIG. 1)

(2HCl salt) mp 180–182° C. (dec.), 85% yield;

$^1$H NMR (2HCl salt) δ1.0 (d, 3H, J=6.7 Hz), 1.1 (d, 3H, J=6.7 Hz), 2.08 (m, 2H), 2.41 (m, 1H), 2.80 (m, 2H), 3.59 (t, 2H, J=5.5 Hz), 4.14 (d, 1H, J=10.0 Hz);

$^{13}$C NMR (2HCl salt) δ22.5, 23.1, 26.7, 28.1, 33.2, 48.9, 62.9, 122.8, 130.6, 150.0;

IR (2HCl salt) 3300, 2770, 1680, 1620, 1575, 1490, 1415, 1332, 1283,1200, 1097, 1031, 747, 694;

MS (m/z, rel. intensity) 195 ($MH^+$, 100), 145 (10), 82 (72), 77 (23).

Imidazoazepine (9e of FIG. 1)

(2HCl salt) mp 179–182° C., 85% yield;

$^1$H NMR (freebase) δ1.75 (m, 2H), 2.58 (m, 2H), 2.71 (m, 1H), 2.80 (dd, 1H, J=13.9, 11 Hz), 3.12 (m, 1H), 3.28 (dd, 1H, J=13.9, 3.3 Hz), 3.95 (dd, 1H, J=10.5, 3.3 Hz), 7.24 (m, 5H);

(2HCl salt) $^1$H NMR δ2.12 (m, 2H), 2.82 (dt, 1H, J=17.0, 4.4 Hz), 2.93 (ddd, 1H, J=17.0, 11.5, 3.5 Hz); 3.28 (dd, 1H, J=13.35, 6.94 Hz), 3.35 (dd, 1H, J=13.35, 9.03 Hz), 3.66 (m, 2H), 4.76 (m, 1H), 7.30 (m, 5H);

$^1$H NMR (2HCl salt) δ7.00, 28.00, 40.80, 48.91, 58.45, 121.87, 130.35, 132.56, 133.79, 134.10, 138.52, 150.00;

IR (2HCl salt) 3000, 2800, 1690, 1550, 1490, 1050, 700;

MS (m/z, rel. intensity) 243 ($MH^+$, 100), 160 (25), 146 (50), 132 (35), 119 (15), 105 (20), 77 (52).

Imidazoazepine (9f of FIG. 1)

(2HCl salt) mp 75–77° C., 85% yield;

$^1$H NMR (freebase) δ0.84 (d, 3H, J=6.3 Hz), 0.89 (d, 3H, J=6.3 Hz), 1.60 (m, 5H), 2.50 (m, 2H), 2.82 (ddd, 1H, J=14.1, 7.2, 3.2 Hz), 3.05 (ddd, 1H, J=14.1, 8.2, 3.0 Hz), 3.76 (dd, 1H, J=8.0, 5.5 Hz);

$^1$H NMR (2HCl salt) δ0.95 (d, 3H, J=6.4 Hz), 0.99 (d, 3H, J=6.4 Hz), 1.72 (m, 2H), 1.96 (m, 2H), 3.57 (m, 2H), 4.57 (t, 1H, J=7.5 Hz);

$^{13}$C NMR (freebase) δ24.6, 26.35, 27.6, 28.4, 31.8, 45.6, 48.7, 56.0, 130.6, 135.1, 150.0;

IR (2HCl salt) 3300, 1700, 1590, 1490, 1410, 1100, 610;

MS (m/z, rel. intensity) 209 ($MH^+$, 100), 195 (12), 151 (8), 102 (5).

Imidazoazepine (9g of FIG. 1)

(2HCl salt) mp 118° C. (dec), (freebase) mp 43–45° C., 85% yield;

$^1$H NMR (freebase) δ1.79 (m, 2H), 2.58 (m, 2H), 2.83 (ddd, 1H, J=13.9, 8.1, 3.6 Hz), 3.21 (ddd, 1H, J=13.9, 6.8, 3.5 Hz), 3.69 (dd, 1H, J=9.4, 8.1 Hz), 3.79 (dd, 1H, J=9.4, 5.2 Hz), 3.97 (dd, 1H, J=7.9, 5.3 Hz), 4.56 (s, 2H), 7.33 (m, 5H);

$^1$H NMR (2HCl salt) δ2.00 (m, 2H), 2.68 (t, 2H, J=6.0 Hz), 3.40 (m, 2H), 3.9 (m, 2H), 4.52 (dd, 1H, J=7.6, 5.0 Hz), 4.64 (dx2, 2H, J=11.7 Hz);

$^{13}$C NMR (2HCl salt) δ26.1, 27.3, 48.1, 57.1, 69.9, 76.4, 122.9, 129.9, 131.8, 131.9, 132.1, 140.1, 150.0;

IR (2HCl salt) 3000, 1678, 1452, 1364, 1320, 1207, 1090, 1025, 912, 746, 700;

MS (m/z, rel. intensity) 301 (12), 273 ($MH^+$, 100), 271 (22), 165 (40), 151 (85), 91 (55), 79 (35).

Imidazoazepine (9h of FIG. 1)

(2HCl salt) mp 175–177° C. (dec.), 85% yield;

$^1$H NMR (2HCl salt) δ2.20 (m, 2H), 2.93 (m, 2H), 3.46 (m, 2H), 5.78 (s, 1H), 7.52 (m, 5H);

$^{13}$C NMR (2HCl salt) δ26.5, 26.6, 49,7, 61.0, 120.7, 129.9, 132.8, 133.6, 134.6, 135.1, 150.0;

IR (2HCl salt) 2950, 2920, 2850, 1680, 1580, 1455, 1376, 702;

MS (m/z, rel. intensity) 229 ($MH^+$, 55), 161 (22), 122 (80), 110 (20), 95 (50), 78 (100).

Imidazoazepine (10h of FIG. 1)

$^1$H NMR (300 MHz, $D_2O$) δ1.78 (m, 1H), 1.97 (m, 1H), 2.63 (m, 2H), 3.15 (m, 1H), 3.87 (m, 1H), 4.42 (dd, J=8.6, 5.6 Hz, 1H), 4.59 (t, J=5.6 Hz, 1H), 4.93 (dd, J=8.6, 5.6 Hz, 1H).

$^{13}$C NMR (100 MHz, $D_2O$) δ26.2, 28.6, 46.9, 57.7, 70.4, 126.7, 131.5, 150.8, 162.5.

MS (DCI, $CH_4$) m/z 209 ($MH^+$).

Ketal (13 of FIG. 2)

A 25 ml acetonitrile solution of trichloroacetylpyrrole (11) (11 mmol) [prepared from (ref. 57: Bailey, D. M., et al., *Journal Of Medicinal Chemistry,* (1973), vol. 16, pages 1300–1302], aminoketal (12) (10 mmol) [commercial], and triethylamine (30 mmol) was stirred at 25° C. for 24 h under argon. The mixture was partitioned between 150 ml of methylene chloride and 100 ml of 5% (aq.) citric acid. The organic layer was washed with sat. $NaHCO_3$ and dried ($MgSO_4$). Concentration afforded a solid which was recrystallized from acetone/methylene chloride to give (13) (80% yield) as a colorless solid, mp 155–157° C.

$^1$H NMR (300 MHz, $CD_3OD$) δ2.73 (td, J=4.7 Hz, 7.1 Hz, 2H), 3.42 (t, J=7.1 Hz, 2H), 3.83 (m, 2H), 3.95 (m, 2H), 4.90 (t, J=4.7 Hz, 1H), 6.76 (s, 1H).

IR (Nujol) $cm^{-1}$ 3358, 3110, 1646, 1569, 1530, 1433, 1412, 1372, 1328, 1244, 1136, 905, 837.

MS (DCI, CH4) m/z 369 ($M^+$+3, 100), 367 ($M^+$+1, 48), 289 (13).

Aldehyde (14 of FIG. 2)

A 70 ml acetone/water (1/1) solution of ketal (13) (10 mmol) and p-toluene sulfonic acid monohydrate (5 mmol) was refluxed for 8 h. The solution was poured into 350 ml of methylene chloride, washed with 100 ml of sat. $NaHCO_3$, and dried over $MgSO_4$. Concentration afforded a solid which was recrystallized from ethyl acetate/methylene chloride to give (14) (85% yield) as a colorless solid, mp 160–163° C.

$^1$H NMR (300 MHz, Acetone-$D_6$) δ2.73 (td, J=6.5 Hz, 1.5 Hz, 2H), 3.63 (q, J=6.5 Hz, 2H), 6.85 (d, J=2.9 Hz, 1H), 7.63 (br, 1H), 9.75 (t, J=1.5 Hz, 1H), 11.73 (br, 1H).

$^{13}$C NMR (300 MHz, Acetone-$D_6$) δ33.9, 44.3, 99.5, 105.6, 113.3, 128.8, 160.3, 201.6.

Bromopyrrole (15 of FIG. 2) ($R_1$=$R_2$=Br)

A solution of aldehyde (14) (10 mmol) in 5 ml of methane sulfonic acid was stirred at 25° C. under argon for 3 days. The reaction mixture neutralized with sat. $NaHCO_3$ and extracted with 200 ml of methylene chloride. The organic layer was dried over $MgSO_4$ and concentrated to afford a solid. Silica gel chromatography of the solid with $CH_2Cl_2$/MeOH($NH_3$), 9/1, as the eluent gave (15) a colorless solid in 82% yield.

mp 172–175° C. (dec).

$^1$H NMR (300 MHz, $CD_3OD$) δ3.57 (d, J=6.4 Hz, 2H), 6.01 (dt, J=10.1 Hz, 6.4 Hz, 1H), 6.65 (d, J=10.1 Hz, 1H).

$^{13}$C NMR (300 MHz, $CD_3OD$) δ39.6, 100.2, 108.4, 126.4, 126.7, 126.8, 127.0, 164.6.

IR (Nujol) cm−$^1$ 3270, 3184, 3020, 1639, 1603, 1541, 1477, 1419, 1265, 1146, 921.

MS (DCI, CH4) m/z 307 ($M^+$+3, 100), 305 ($M^+$+1, 55), 278 (20), 264 (22).

(±)-Hymenin (16 of FIG. 2) (From Pyrrole (15 of FIG. 2))

A solution of aldehyde (14) ((14) is also called a pyrrole) (10 mmol) and 2-aminoimidazole sulfate (12 mmol) in 5 ml of methane sulfonic acid was stirred at 25° C. under argon for 5 days. The reaction was neutralized with sat. $NaHCO_3$ and concentrated to afford a solid. The solid was taken up in 75 ml of ethanol, filtered and the filtrate was concentrated. Silica gel chromatography of the resulting residue with $CH_2Cl_2$/MeOH($NH_3$), 8/2, afforded a 76% yield of (±)-hymenin (16) as a solid, mp 86–9020 C. (dec), $^1$H NMR (300 MHz, $CD_3OD$) δ1.92 (m,1H), 2.25 (m, 1H), 3.06 (dd, J=14.0 Hz, 7.3 Hz, 1H), 3.16 (dd, J=14.0 Hz, 9.8 Hz, 1H), 4.12 (t, J=3.5 Hz, 1H), 5.88 (s, 1H)

$^{13}$C NMR (300 MHz, $CD_3OD$) 32.7, 37.9, 38.4, 102.8, 107.7, 113.0, 125.3, 128.5, 136.8, 150.6, 164.2.

IR (Nujol) cm$^{-1}$ 3360, 3270, 3150, 1676, 1625, 1566, 1481, 1425, 1327, 1216, 1095, 949.

MS (DCI, $CH_4$) m/z 390 ($M^+$+3, 50), 388 ($M^+$+1, 35), 312 (22), 112 (100).

(±)-Hymenin (16 of FIG. 2) (From Aldehyde 14 of FIG. 2)

The process described here for (±)-Hymenin (16) (From Aldehyde (14)) represents the most preferable process. A solution of aldehyde (14) (10 mmol) and 2-aminoimidazole sulfate (12 mmol) in 5 ml of methane sulfonic acid was stirred at 25° C. under argon for 5 days. The reaction was neutralized with sat. $NaHCO_3$ and concentrated to afford a solid. The solid was taken up in 75 ml of ethanol, filtered and the filtrate was concentrated. Silica gel chromatography of the resulting residue with $CH_2Cl_2$/MeOH($NH_3$), 8/2, afforded a 63% yield of (±)-hymenin (16) as a solid, mp 86–90° C. (dec), $^1$H NMR (300 MHz, $CD_3OD$) δ1.92 (m,1H), 2.25 (m, 1H), 3.06 (dd, J=14.0 Hz, 7.3 Hz, 1H), 3.16 (dd, J=14.0 Hz, 9.8 Hz, 1H), 4.12 (t, J=3.5 Hz, 1H), 5.88 (s, 1H)

$^{13}$C NMR (300 MHz, $CD_3OD$) 32.7, 37.9, 38.4, 102.8, 107.7, 113.0, 125.3, 128.5, 136.8, 150.6, 164.2.

IR (Nujol) cm$^{-1}$ 3360, 3270, 3150, 1676, 1625, 1566, 1481, 1425, 1327, 1216, 1095, 949.

MS (DCI, $CH_4$) m/z 390 ($M^+$+3, 50), 388 ($M^+$+1, 35), 312 (22), 112 (100).

Figure 4:
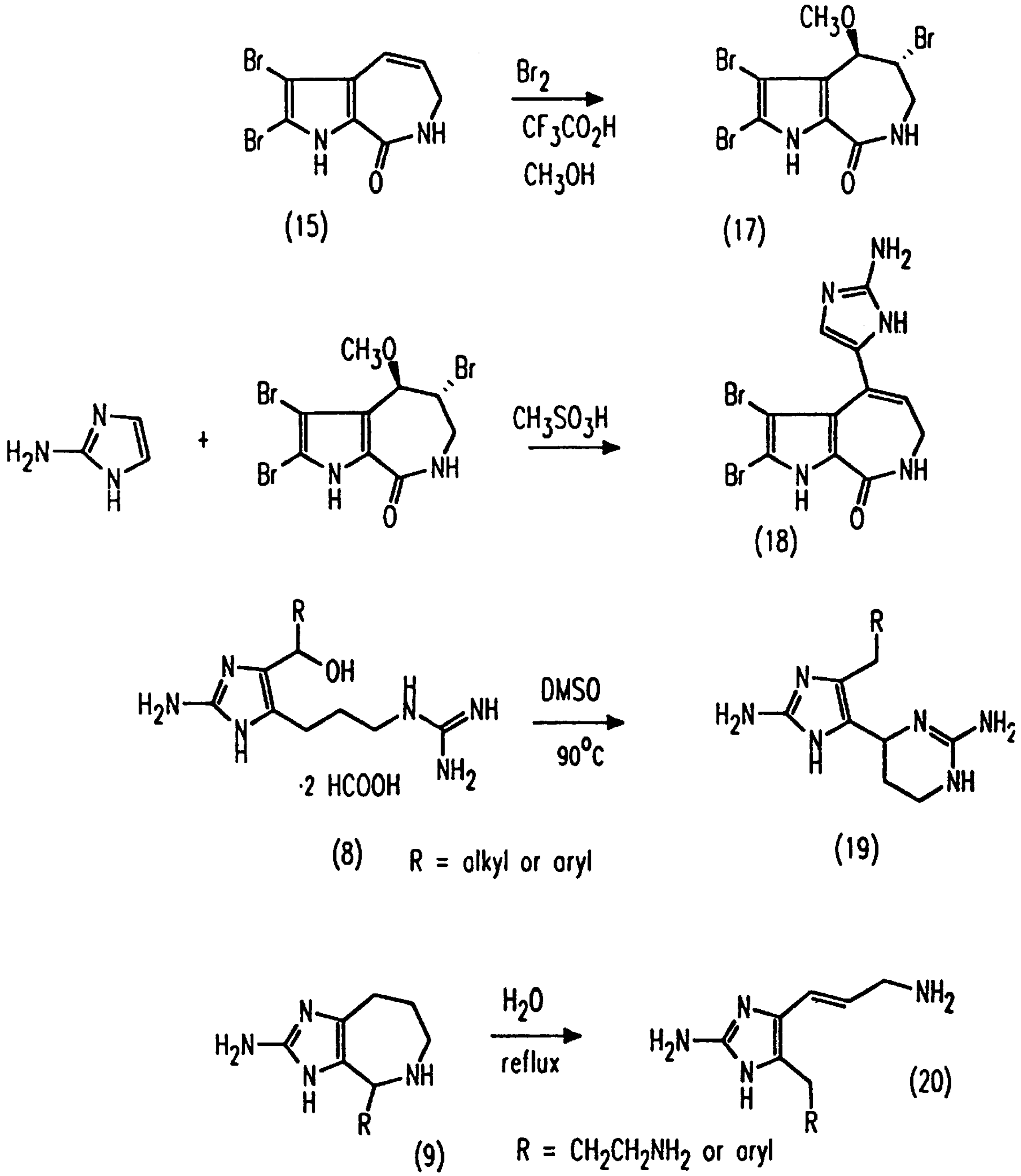
FIG. 4 depicts the synthesis of odiline (18), and aminoimidazoles 19 amd 20.

Odiline (18 of FIG. 4) (From pyrrole 17 of FIG. 4, prepared from pyrrole 15)

Compound 17 was prepared as follows: To a solution of compound (1 mmol; 15 in FIG. 2A, $R_A$=$R_B$=Br) in trifluoroacetic acid was added bromine (1 mmol) at 25° C. The mixture was sirred for 1 h and then concentrated. The resulting residue was taken up in methanol and evaporated. This was repeated three times to remove trifluoroacetic acid. Complete removal of the methanol afforded 17 as a solid pure enough for the next step.

A solution of pyrrole 17 and 2-aminoimidazole was heated at 80° C. in methanesulfonic acid for 3 days. After this time, the reaction was cooled to 25° C. and the product was precipitated with diethyl ether. Silica gel chromatography of the precipitate was carried out using methylene chloride/methanol (saturated with ammonia; 8:2) afforded odiline (18) in 60% yield as a pure solid.

Aminoimidazole 19 (from aminoimidazole 8 of FIG. 1(C))

This method was used to prepare aminoimidazole 19 wherein R is methyl and chloromethyl. The method is also used to prepare aminoimidazole 19 wherein R is phenyl.

A solution of aminoimidazole 8 in dimethyl sulfoxide was heated at 90° C. for 3 h. The reaction was cooled to 25° C., and triturated with diethyl ether. Silica gel chromatography of the resulting residue using formic acid/water/ethanol (0.5:0.5:9) afforded pure compound 19 in 90% yield as its formic acid salt.

Aminoimidazole 20 (from aminoimidazole 9 of FIG. 1(D))

This method was used to prepare aminoimidazole 20 wherein R is phenyl, p-chlorophenyl, p-methoxyphenyl and p-toluyl.

A solution of aminoimidazole 9 in water was refluxed for 12 h. The reaction was concentrated, and the residue was purifed by silica gel chromatography using methylene chloride/methanol (sat. ammonia) (8:2) as eluant affording compound 20 in 60% yield.

LIST OF REFERENCES

1. Chevolot, L., in *Marine Natural Products: Chemical And Biological Perspectives,* Scheuer, P. J., editor; John Wiley and Sons, New York, (1981), vol. 4, pages 53–91.
2. Christophersen, C., in *The Alkaloids: Chemistry And Pharmacology,* Brossi, A., editor; Academic Press, Inc., New York, (1985), vol. 24, pages 25–111.
3. Fenical, W., in *Alkaloids: Chemical And Biological Perspectives,* Pelletier, S. W., editor; John Wiley and Sons, New York, (1986), vol. 4, pages 275–330.
4. Faulkner, D. J., *Natural Product Reports,* (1991), vol. 8, pages 97–147, and earlier reports.
5. Kobayashi, J., et al., *Experientia,* (1986), vol. 42, pages 1176–1177.
6. Kobayashi, J., et al., *Experientia,* (1988), vol. 44, pages 86–87.
7. Rinehart, K. L., et al., *Journal Of Natural Products,* (1990), vol. 53, pages 771–792.
8. Pettit, G. R., et al., *Canadian Journal Of Chemistry,* (1990), vol. 68, pages 1621–1624.

9. Kobayashi, J., et al., *Tetrahedron,* (1990), vol. 46, pages 5579–5586.
10. Kobayashi, J., et al., *Experientia,* (1991), vol. 47, pages 301–304.
11. Commercon, A., et al., *Tetrahedron Letters,* (1991), vol. 32, pages 1419–1422.
12. Dalkafouki A., et al., *Tetrahedron Letters,* (1991), vol. 32, pages 5325–5328.
13. Cariello, L., et al., *Journal Of The Chemical Society Chemical Communications,* (1973), pages 99–100.
14. Cariello, L., et al., *Tetrahedron,* (1974), vol. 30, pages 3281–3287.
15. Cariello, L., et al., *Experientia,* (1974), vol. 30, pages 849–850.
16. Cariello, L., et al., *Tetrahedron,* (1974), vol. 30, pages 3611–3614.
17. Cariello, L., et al., *Tetrahedron,* (1974), vol. 30, pages 4191–4196.
18. Cariello, L., et al., *Comparative Biochemistry and Physiology,* (1979), vol. 63B, pages 77–82.
19. Schwartz, R. E., et al., *Tetrahedron Letters,* (1978), pages 2235–2238.
20. Schwartz, R. E., et al., *Canadian Journal Of Chemistry,* (1979), vol. 57, pages 1707–1711.
21. Komoda, Y., et al., *Chemical & Pharmaceutical Bulletin,* (1975), vol. 23, pages 2464–2465.
22. Komoda, Y., et al., *Chemical & Pharmaceutical Bulletin,* (1982), vol. 30, pages 502–508.
23. Quadrifoglio, F., et al., *Chemico-Biological Interactions,* (1975), vol. 11, pages 91–99.
24. Prota, G., in *Marine Natural Products: Chemical And Biological Perspectives,* Scheuer, P. J., editor; Academic Press, New York, (1980), vol. 3, pages 141–178.
25. Cimino, G., et al., *Comparative Biochemistry And Physiology,* (1974), vol. 47B, pages 895–897.
26. Remers, W. A., in *The Chemistry Of Heterocyclic Compounds: Indoles Part I,* Houlihan, W. J., editor; Wiley-Interscience, New York, (1972), pages 66–70.
27. Chadwick, D. J., in *Comprehensive Heterocyclic Chemistry: The Structure, Reactions, Synthesis And Uses Of Heterocyclic Compounds,* Katritzky, A. R., and Rees, C. W., editorial board; Bird, C. W., and Cheeseman, W. H., editors; Pergamon Press, New York, (1984), vol. 4, part 3, pages 206–209.
28. Braun, M., et al., *Journal Of The American Chemical Society,* (1976), vol. 98, pages 3049–3050.
29. Braun, M., et al., *Journal Of The American Chemical Society,* (1978), vol. 100, page 4208–4212.
30. Kenyon, G. L., et al., *Journal Of The American Chemical Society,* (1971), vol. 93, pages 5552–5560.
31. Seki, Y., et al., *The Journal Of Biochemistry,* (Tokyo, Japan), (1970), vol. 67, pages 389–396.
32. Hill, R. K., "The Imidazole Alkaloids," in *Alkaloids: Chemical And Biological Perspectives,* Pelletier, S. W., editor; vol. 2, John Wiley and Sons, Inc., New York, (1984), pages 49–104.
33. Kobayashi, J., et al., *Experientia,* (1986), vol. 42, pages 1064–1065.
34. Sharma, G. M., et al., *Journal Of The Chemical Society Chemical Communications,* (1980), pages 435–436.
35. Cimino, G., et al., *Tetrahedron Letters,* (1982), vol. 23, pages 767–768.
36. Kitagawa, I., et al., *Chemical & Pharmaceutical Bulletin,* (1983), vol. 31, pages 2321–2328.
37. De Nanteuil, G., et al., *Tetrahedron,* (1985), vol. 41, pages 6019–6033.
38. Walker, R. P., et al., *Journal Of The American Chemical Society,* (1981), vol. 103, pages 6772–6773.
39. Rinehart, K. L., Jr., U.S. Pat. No. 4,737,510 (Apr. 12, 1988), page 12.
40. Rinehart, K. L., *Pure And Applied Chemistry,* (1989), vol. 61, pages 525–528.
41. Ahond, A., et al., *Séances Acad. Sci. Paris,* (1988) vol. 307, (série 2), page 145.
42. Zurita, M. B., et al., *Tetrahedron,* (1989), vol. 45, pages 6713–6720.
43. Commercon, A., et al., *Tetrahedron Letters,* (1990), vol. 31, pages 3871–3874.
44. Hall, S., et al., *The Saxitoxins,* S. Hall, et al., editors; ACS Symposium Series 418, "Marine Toxins, Origin, Structure And Molecular Pharmacology," American Chemical Society, Washington, D.C., (1990), page 29.
45. Shimizu, Y., *Annals Of The New York Academy Of Sciences,* (1986), vol. 479, pages 24–31.
46. Kao, C. Y., *Annals Of The New York Academy Of Sciences,* (1986), vol. 479, pages 52–67.
47. Tanino, H., et al., *Journal Of The American Chemical Society,* (1977), vol. 99, pages 2818–2819.
48. Kishi, Y., *Heterocycles,* (1980), vol. 14, pages 1477–1495.
49. Faulkner, D. J., "Brominated Marine Natural Products," in *Bromine Compounds: Chemistry And Applications,* D. Price, et al., editors, Elsevier, N.Y. (1988), page 121.
50. Fukuzawa, A., et al., *Chemistry Letters,* (1990), pages 1287–1290.
51. Palmer, B. D. et al., *Journal Of The Chemical Society Perkin Transactions I,* (1989), vol. 95.
52. Stensio, K. E., et al., *Acta Chemica Scandinavica,* (1973), vol. 27, pages 2179–2183.
53. Calo, V., et al., *Journal Of The Chemical Society Perkin Transactions I,* (1972), no. 20, pages 2567–2568.
54. Lancini, G. C., et al., *Journal Of Heterocyclic Chemistry,* (1966), vol. 3, pages 152–154.
55. Lancini, G., et al., British Patent 1,132,013, (1968).
56. McClelland, R. A., et al., *Journal Of The American Chemical Society,* (1987), vol. 109, pages 4308–4314.
57. Bailey, D. M., et al., *Journal Of Medicinal Chemistry,* (1973), vol. 16, pages 1300–1302.
58. Hodge, P., et al., *Journal Of The Chemical Society,* (1965), pages 459–470.
59. Anderson, H. J., et al., *Canadian Journal Of Chemistry,* (1965), vol. 43, pages 409–414.
60. Sharma, G. M., et al., *Journal Of The Chemical Society Chemical Communications,* (1971), no. 3, pages 151–152.
61. Sharma, G., et al., *The Journal Of Organic Chemistry,* (1977), vol. 42, pages 4118–4124.
62. Fedoreyev, S. A., et al., *Tetrahedron Letters,* (1986), vol. 27, pages 3177–3180.
63. Forenza, S., et al., *Journal Of The Chemical Society Chemical Communications,* (1971), no. 18, pages 1129–1130.
64. Garcia, E. E., et al., *Journal Of The Chemical Society Chemical Communications,* (1973), no. 3, pages 78–79.
65. Albizati, K. F., et al., *The Journal Of Organic Chemistry,* (1985), vol. 50, pages 4163–4164.
66. Heath, H., et al., *Journal Of The Chemical Society,* (1951), pages 2223–2225.
67. Foster, A. B., et al., *Journal Of Medicinal Chemistry,* (1981), vol. 24, pages 1399–1403.
89. Sehgal, R. K., et al., *Journal Of Heterocyclic Chemistry,* (1979), vol. 16, pages 871–876.
69. Heath, H., et al., *Journal Of The Chemical Society,* (1951), pages 2217–2220.
70. Grimmett, M. R., *Comprehensive Heterocyclic Chemistry: The Structure, Reactions, Synthesis And Uses Of*

*Heterocyclic Compounds,* Potts, K. T., editor; Pergamon Press; New York, (1984), vol. 5, pages 404–405.

What is claimed is:

1. A compound having the structure:

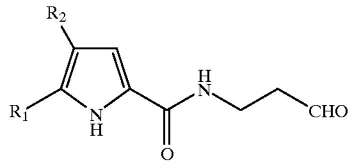

wherein $R_1$ and $R_2$ are the same or different, and are H; a $C_1$ to about $C_{10}$ straight chain alkyl group or branched alkyl group, which alkyl groups are substituted or unsubstituted; or halogen.

2. The compound of claim 1 having the structure:

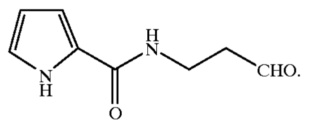

3. The compound of claim 1 having the structure:

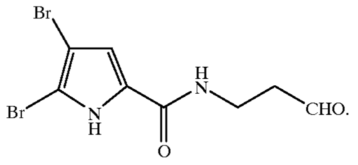

4. The compound of claim 3, wherein the alkyl groups are substituted with halogen, alcohol, alkoxy, dialkyl amine, alkyl aryl amine, diaryl amine, thiol, or sulfide groups.

5. The process for preparing the compound of claim 1, wherein $R_1$ and $R_2$ are the same as defined for the compound, which process comprises:

reacting one molecular equivalent of a ketal having the structure

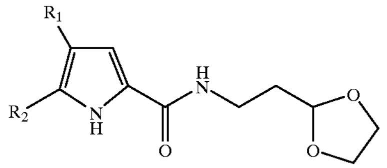

with 0.5 molecular equivalent of p-toluene sulfonic acid monohydrate, at a temperature of about 0° C. to about 100° C.;

in a solvent, wherein the solvent is a mixture of water and a polar nonhydroxylic organic solvent, and the volume ratio of the water and the polar nonhydroxylic organic solvent is from about 1/10 to about 10/1;

to form the compound.

6. The process of claim 5, wherein the polar nonhydroxylic organic solvent is N,N-dimethylformamide; dioxane; tetrahydrofuran; dimethylsulfoxide; or acetonitrile.

7. The process of claim 5, wherein the volume ratio of the water and the polar nonhydroxylic organic solvent is from about 40/60 to about 60/40.

8. The process of claim 5, wherein the solvent is a mixture of water and acetone in a volume ratio of from about 40/60 to about 60/40.

9. The process of claim 5, wherein the temperature is about 80° C. to about 100° C.

10. The process of claim 5, wherein the process is performed for a reaction time of from about 3 hours to about 24 hours.

11. The process of claim 5, wherein the process is performed for a reaction time of from about 6 hours to about 10 hours.

12. A ketal aminoimidazole compound having the structure:

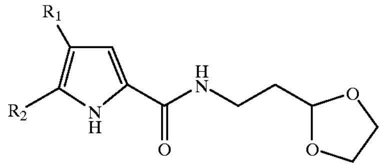

wherein $R_1$ and $R_2$ are the same or different, and are H; a $C_1$ to about $C_{10}$ straight chain alkyl group or branched alkyl group, which alkyl groups are substituted or unsubstituted; or halogen.

13. The ketal aminoimidazole compound of claim 12, wherein the alkyl groups are substituted with halogen, alcohol, alkoxy, dialkyl amine, alkyl aryl amine, diaryl amine, thiol, or sulfide groups.

14. The compound of claim 12 having the structure:

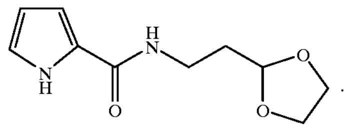

15. The compound of claim 12, having the structure:

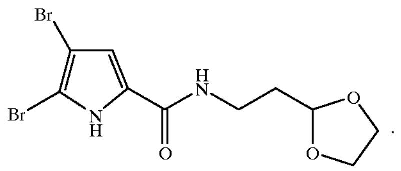

* * * * *